US011166712B2

(12) United States Patent
Nobles et al.

(10) Patent No.: US 11,166,712 B2
(45) Date of Patent: *Nov. 9, 2021

(54) SUTURING DEVICES AND METHODS FOR SUTURING AN ANATOMIC VALVE

(71) Applicant: Scarab Technology Services, LLC, St. Thomas, VI (US)

(72) Inventors: Anthony A. Nobles, Fountain Valley, CA (US); Benjamin G. Brosch, Mission Viejo, CA (US); John R. Crew, San Francisco, CA (US)

(73) Assignee: Scarab Technology Services, LLC, St. Thomas (VG)

( * ) Notice: Subject to any disclaimer, the term of this patent is extended or adjusted under 35 U.S.C. 154(b) by 229 days.

This patent is subject to a terminal disclaimer.

(21) Appl. No.: 16/370,198

(22) Filed: Mar. 29, 2019

(65) Prior Publication Data

US 2019/0388084 A1    Dec. 26, 2019

Related U.S. Application Data

(63) Continuation of application No. 15/058,236, filed on Mar. 2, 2016, now Pat. No. 10,285,687, which is a
(Continued)

(51) Int. Cl.
*A61B 17/04*    (2006.01)
*A61B 17/06*    (2006.01)

(52) U.S. Cl.
CPC ...... *A61B 17/0469* (2013.01); *A61B 17/0482* (2013.01); *A61B 17/04* (2013.01);
(Continued)

(58) Field of Classification Search
CPC . A61B 17/0057; A61B 17/04; A61B 17/0401; A61B 17/0409; A61B 17/0469;
(Continued)

(56) References Cited

U.S. PATENT DOCUMENTS

| 118,683 A | 9/1871 | Bruce |
|---|---|---|
| 1,064,307 A | 6/1913 | Fleming |

(Continued)

FOREIGN PATENT DOCUMENTS

| AU | 2003212025 | 8/2003 |
|---|---|---|
| AU | 2006251579 | 11/2006 |

(Continued)

OTHER PUBLICATIONS

U.S. Appl. No. 13/736,032, filed Jan. 7, 2013, Nobles et al.
(Continued)

*Primary Examiner* — Robert A Lynch
(74) *Attorney, Agent, or Firm* — Knobbe, Martens, Olson & Bear LLP

(57) ABSTRACT

A device for suturing an anatomic valve can comprise an elongate body, a suture catch mechanism and a suture clasp arm. The suture catch mechanism can be operatively coupled to the elongate body for movement between a retracted position and an advanced position. The suture clasp arm can be attached to the elongate body for movement between a retracted position and an extended position. The suture clasp arm can comprise a suture clasp configured to releasably retain a suture portion. In some embodiments, the suture clasp is positioned on the suture clasp arm such that the suture catch mechanism retrieves the suture portion from the suture clasp arm while the arm is at least partially retracted. In some embodiments, the suture clasp arm can be closed about a tissue portion without damaging the tissue portion.

20 Claims, 42 Drawing Sheets

Related U.S. Application Data continuation of application No. 14/311,518, filed on Jun. 23, 2014, now Pat. No. 9,326,764, which is a continuation of application No. 12/463,046, filed on May 8, 2009, now Pat. No. 8,771,296.

(60) Provisional application No. 61/052,146, filed on May 9, 2008.

(52) U.S. Cl.
CPC . *A61B 2017/047* (2013.01); *A61B 2017/0472* (2013.01); *A61B 2017/0488* (2013.01); *A61B 2017/06042* (2013.01); *A61B 2017/06057* (2013.01)

(58) Field of Classification Search
CPC ............ A61B 17/0482; A61B 17/0483; A61B 17/0491; A61B 17/08; A61B 2017/00243; A61B 2017/00353; A61B 2017/00575; A61B 2017/00637; A61B 2017/00641; A61B 2017/00663; A61B 2017/047; A61B 2017/0472; A61B 2017/0488; A61B 2017/081; A61F 2/2463; A61F 2/2466

See application file for complete search history.

(56) References Cited

U.S. PATENT DOCUMENTS

| | | |
|---|---|---|
| 1,593,347 A | 7/1926 | Nardi |
| 1,822,330 A | 9/1931 | Ainslie |
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,601,564 A | 6/1952 | Smith |
| 2,637,290 A | 5/1953 | Sigoda |
| 2,738,790 A | 3/1956 | Todt, Sr. et al. |
| 2,741,225 A | 4/1956 | Fink |
| 2,741,226 A | 4/1956 | Dietrich et al. |
| 2,748,748 A | 6/1956 | Lovejoy |
| 2,790,422 A | 4/1957 | Grumbach |
| 2,849,002 A | 8/1958 | Oddo |
| 2,945,460 A | 7/1960 | Kagiyama |
| 2,959,172 A | 11/1960 | Held |
| 2,988,055 A | 6/1961 | Platt |
| 3,098,467 A | 7/1963 | Nagele, Jr. |
| 3,107,654 A | 10/1963 | Fehrenback |
| 3,241,554 A | 3/1966 | Coanda |
| 3,260,242 A | 7/1966 | Liguori |
| 3,262,427 A | 7/1966 | Von Arx |
| 3,292,627 A | 12/1966 | Harautuneian |
| 3,294,068 A | 12/1966 | Hechtle |
| 3,301,221 A | 1/1967 | Von Arx |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 3,989,389 A | 11/1976 | Hashimoto et al. |
| 4,022,535 A | 5/1977 | Ritter |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,168,708 A | 9/1979 | Lepley et al. |
| 4,204,541 A | 5/1980 | Kapitanov |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,641,652 A | 2/1987 | Hutterer et al. |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,904,238 A | 2/1990 | Williams |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,946,463 A | 8/1990 | Wright |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,988,339 A | 1/1991 | Vadher |
| 4,994,070 A | 2/1991 | Waters |
| 5,002,531 A | 3/1991 | Bonzel |
| 5,021,059 A | 6/1991 | Kensey et al. |
| 5,037,428 A | 8/1991 | Picha et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,108,421 A | 4/1992 | Fowler |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,152,769 A | 10/1992 | Baber |
| 5,160,339 A | 11/1992 | Chen et al. |
| 5,163,906 A | 11/1992 | Ahmadi |
| 5,167,223 A | 12/1992 | Koros et al. |

(56) References Cited

U.S. PATENT DOCUMENTS

| | | |
|---|---|---|
| 5,171,251 A | 12/1992 | Bregen et al. |
| 5,171,259 A | 12/1992 | Inoue |
| 5,176,691 A | 1/1993 | Pierce |
| 5,192,301 A | 3/1993 | Kamiya et al. |
| 5,196,025 A | 3/1993 | Ranalletta et al. |
| 5,201,760 A | 4/1993 | West |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,254,126 A | 10/1993 | Filipi et al. |
| 5,269,791 A | 12/1993 | Mayzels et al. |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,323,789 A | 6/1994 | Berggren et al. |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,387,221 A | 2/1995 | Bisgaard |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,568 A | 12/1995 | Scott |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,503,634 A | 4/1996 | Christy |
| 5,507,754 A | 4/1996 | Green et al. |
| 5,507,755 A | 4/1996 | Gresl et al. |
| 5,507,757 A | 4/1996 | Sauer et al. |
| 5,514,159 A | 5/1996 | Matula et al. |
| 5,520,609 A | 5/1996 | Moll et al. |
| 5,520,702 A | 5/1996 | Sauer et al. |
| 5,520,703 A | 5/1996 | Essig et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,618 A | 8/1996 | Fleenor et al. |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,685 A | 10/1996 | Mollenauer et al. |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,571,167 A | 11/1996 | Maginot |
| 5,573,540 A | 11/1996 | Yoon |
| 5,578,044 A | 11/1996 | Gordon et al. |
| 5,584,803 A | 12/1996 | Stevens et al. |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,662,664 A | 9/1997 | Gordon et al. |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A | 12/1997 | Buelna et al. |
| 5,700,276 A | 12/1997 | Benecke |
| 5,700,277 A | 12/1997 | Nash et al. |
| 5,707,379 A | 1/1998 | Fleenor et al. |
| 5,709,693 A | 1/1998 | Taylor |
| 5,713,910 A | 2/1998 | Gordon et al. |
| 5,716,329 A | 2/1998 | Dieter |
| 5,720,757 A | 2/1998 | Hathaway et al. |

(56) References Cited

U.S. PATENT DOCUMENTS

| | | |
|---|---|---|
| 5,722,983 A | 3/1998 | Van Der Weegen |
| 5,728,109 A | 3/1998 | Schulze et al. |
| 5,728,133 A | 3/1998 | Kontos |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,836,956 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,868,764 A | 2/1999 | Rosengart |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,924,424 A | 7/1999 | Stevens et al. |
| 5,925,054 A | 7/1999 | Taylor et al. |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,947,919 A | 9/1999 | Krueger et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,042,601 A | 3/2000 | Smith |
| 6,048,351 A | 4/2000 | Gordon et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,276 A | 6/2000 | Kontos |
| 6,077,277 A | 6/2000 | Mollenauer et al. |
| 6,086,608 A | 7/2000 | Ek et al. |
| 6,099,553 A | 8/2000 | Hart et al. |
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,165,196 A | 12/2000 | Stack et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,482,171 B1 | 11/2002 | Corvi et al. |
| 6,508,777 B1 | 1/2003 | Macoviak et al. |
| 6,527,785 B2 | 3/2003 | Sancoff et al. |
| 6,533,795 B1 * | 3/2003 | Tran .............. A61B 17/0469 606/144 |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,695,859 B1 | 2/2004 | Golden et al. |
| 6,712,831 B1 | 3/2004 | Kaplan et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B1 | 9/2004 | Sancoff |
| 6,978,176 B2 | 1/2005 | Lattouf |
| 6,855,157 B2 | 2/2005 | Foerster et al. |
| 6,887,249 B1 | 5/2005 | Houser et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 6,964,668 B2 | 11/2005 | Modesitt et al. |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |

(56) References Cited

U.S. PATENT DOCUMENTS

| | | |
|---|---|---|
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,197,510 B2 | 6/2012 | Nobles |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,709,020 B2 | 4/2014 | Nobles |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 2001/0021854 A1 | 9/2001 | Donnez et al. |
| 2001/0031973 A1 | 10/2001 | Nobles et al. |
| 2001/0049492 A1 | 12/2001 | Frazier et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0087178 A1 | 7/2002 | Nobles et al. |
| 2002/0096183 A1 | 7/2002 | Stevens et al. |
| 2002/0111653 A1 | 8/2002 | Foerster |
| 2002/0128598 A1 | 9/2002 | Nobles |
| 2002/0128684 A1 | 9/2002 | Foerster |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0144673 A1 | 7/2003 | Onuki et al. |
| 2003/0149448 A1 | 8/2003 | Foerster et al. |
| 2003/0167062 A1 | 9/2003 | Gambale et al. |
| 2003/0171760 A1 | 9/2003 | Gambale |
| 2003/0181926 A1 | 9/2003 | Dana et al. |
| 2003/0195539 A1 | 10/2003 | Attinger et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1* | 3/2004 | Eigler ............... A61B 17/0469 606/148 |
| 2004/0068273 A1 | 4/2004 | Fariss et al. |
| 2004/0093031 A1 | 5/2004 | Burkhart et al. |
| 2004/0097968 A1 | 5/2004 | Sikikhman et al. |
| 2004/0102797 A1 | 5/2004 | Golden et al. |
| 2004/0098050 A1 | 8/2004 | Foerster et al. |
| 2004/0153116 A1 | 8/2004 | Nobles |
| 2004/0210238 A1 | 10/2004 | Nobles et al. |
| 2004/0236356 A1 | 11/2004 | Rioux et al. |
| 2004/0260298 A1 | 12/2004 | Kaiseer et al. |
| 2005/0033319 A1 | 2/2005 | Gambale et al. |
| 2005/0033361 A1 | 2/2005 | Galdonik et al. |
| 2005/0070923 A1 | 3/2005 | McIntosh |
| 2005/0149066 A1* | 7/2005 | Stafford ............ A61B 17/0469 606/144 |
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0240226 A1 | 10/2005 | Foerster et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2005/0288688 A1 | 12/2005 | Sakamoto et al. |
| 2005/0288690 A1 | 12/2005 | Bourque et al. |
| 2006/0047314 A1 | 3/2006 | Green |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0271074 A1 | 11/2006 | Ewers et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0005081 A1 | 1/2007 | Findlay, III et al. |
| 2007/0010829 A1 | 1/2007 | Nobles et al. |
| 2007/0032798 A1 | 2/2007 | Pantages et al. |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0234729 A1 | 9/2008 | Page et al. |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |

(56) References Cited

U.S. PATENT DOCUMENTS

| | | |
|---|---|---|
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0202077 A1 | 8/2011 | Chin et al. |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0238001 A1 | 9/2013 | Nobles et al. |
| 2013/0261645 A1 | 10/2013 | Nobles et al. |
| 2013/0324800 A1 | 12/2013 | Cahill |
| 2014/0148825 A1 | 5/2014 | Nobles et al. |
| 2014/0163585 A1 | 6/2014 | Nobles et al. |
| 2014/0303654 A1 | 10/2014 | Nobles et al. |
| 2014/0309670 A1 | 10/2014 | Bakos et al. |
| 2014/0379006 A1 | 12/2014 | Sutherland et al. |
| 2015/0359531 A1 | 12/2015 | Sauer |
| 2016/0151064 A1 | 6/2016 | Nobles |
| 2016/0302787 A1 | 10/2016 | Nobles |
| 2017/0035425 A1 | 2/2017 | Fegelman et al. |
| 2017/0049451 A1 | 2/2017 | Hausen |
| 2017/0296168 A1 | 4/2017 | Nobles et al. |
| 2017/0128059 A1 | 5/2017 | Coe et al. |
| 2017/0245853 A1 | 8/2017 | Nobles |
| 2017/0303915 A1 | 10/2017 | Nobles |
| 2019/0029672 A1 | 1/2019 | Nobles et al. |
| 2019/0239880 A1 | 8/2019 | Nobles |

FOREIGN PATENT DOCUMENTS

| | | |
|---|---|---|
| AU | 2006262498 | 1/2007 |
| CA | 2323084 | 12/2006 |
| CN | 195341 | 2/2005 |
| CN | 1654016 A | 8/2005 |
| CN | 101027001 | 8/2007 |
| CN | 101242785 A | 8/2008 |
| CN | 101495049 | 12/2010 |
| CN | 101257852 | 8/2011 |
| CN | ZL 201280029608.6 | 10/2016 |
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 0 983 026 | 3/2002 |
| EP | 1 196 093 | 4/2002 |
| EP | 1 303 218 | 4/2003 |
| EP | 0 941 698 | 5/2005 |
| EP | 0 870 486 | 11/2005 |
| EP | 0 983 027 | 12/2005 |
| EP | 1 804 677 | 7/2007 |
| EP | 1 852 071 | 11/2007 |
| EP | 1 570 790 | 11/2008 |
| EP | 1 987 779 | 11/2008 |
| EP | 2 011 441 | 1/2009 |
| EP | 2 572 649 | 3/2013 |
| FR | 2 701 401 | 8/1994 |
| HK | 1036395 | 5/2005 |
| JP | A 9507398 | 7/1997 |
| JP | 09-266910 A | 10/1997 |
| JP | H10-43192 | 2/1998 |
| JP | 2001-524864 | 12/2001 |
| JP | 2002-500531 | 1/2002 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 4399035 | 10/2009 |
| JP | 2009-261960 | 11/2009 |
| JP | 2010-522625 | 7/2010 |
| JP | 2011-067251 | 4/2011 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/25254 | 5/1999 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |
| WO | WO 09/137766 | 11/2009 |
| WO | WO 11/094619 | 8/2011 |
| WO | WO 11/137224 | 11/2011 |
| WO | WO 12/012336 | 1/2012 |
| WO | WO 12/142338 | 10/2012 |
| WO | WO 13/027209 | 2/2013 |
| WO | WO 13/142487 | 9/2013 |
| WO | WO 13/170081 | 11/2013 |
| WO | WO 15/002815 | 1/2015 |
| WO | WO 15/085145 | 6/2015 |
| WO | WO 17/180092 | 10/2017 |
| WO | WO 19/035095 | 2/2019 |
| WO | WO 19/051379 | 3/2019 |
| WO | WO 19/055433 | 3/2019 |

OTHER PUBLICATIONS

U.S. Appl. No. 14/400,309, filed Nov. 10, 2014, Nobles et al.
U.S. Appl. No. 09/080,823, filed May 18, 1998, Nobles.
U.S. Appl. No. 09/080,436, filed May 18, 1999, Nobles.
U.S. Appl. No. 16/161,610, filed Oct. 16, 2018, Nobles et al.
Advances in Vascular Surgery, by John S. Najarian, M.D. and John

(56) References Cited

OTHER PUBLICATIONS

P. Delaney, M.D., copyright 1983 by Year Book Publishers, Inc. at pp. 94,95,96, and 224.
Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.
Current Therapy in Vascular Surgery, 2nd edition, by Calvin B. Ernst, M.D. and James C. Stanley, M.D., copyright 1991 By B.C. Decker, Inc., at pp. A and 140.
Eskuri, A., The Design of a Minimally Invasive Vascular Suturing Device, Thesis submitted to Rose-Hulman Institute of Technology, Nov. 1999.
Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.
Nursing the Open-Heart Surgery Patient, By Mary Jo Aspinall, R.N., M.N., copyright 1973 by McGraw Hill, Inc., at pp. 216 and 231.
Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.
Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.
Techniques in Vascular Surgery, by Denton A. Cooley, MD. and Don C. Wukasch, MD., copyright 1979 by WB. Saunders Co., at pp. 38,57,86,134,156, and 184.
Vascular Access, Principles and Practice, 3rd edition, by Samuel Eric Wilson, MD., copyright 1996, 1988,1980 by Mosby-Year Book, Inc., pp. 89 and 159.
Vascular and Endovascular Surgery, by Jonathan D. Beard and Peter Gainers, copyright 1998 by W. B. Saunders Co., Ltd, p. 414.
Vascular Surgery, 3rd edition, vol. 1, by Robert B. Rutherford, MD., copyright 1989, 1984, 1976 By W. B.SaundersCo., at pp. 347, 348, 354, 594, 607, 622, 675, 677, 680, 698, 700, 721, 727, 735, and 829.
Vascular Surgery, 4th edition by Robert B. Rutherford, MD., copyright 1995,1989,1976, by W.B. Saunders Co., vol. 1, at pp. 400-404, 661, and A.
Vascular Surgery, 4th edition, by Robert B. Rutherford, M.D., copyright 1995, 1989, 1984, 1976 by W. B. Saunders Co., vol. 2, at pp. 1318, 1363, 1426, 1564, and 1580.
Vascular Surgery, by Robert B. Rutherford, M.D. copyright1977 by WB. Saunders Co., at pp. 334 and 817.
European Examination Report, re EP Application No. 09 743 742.9, dated Apr. 18, 2102.
Japanese Office Action (Decision of Rejection) dated Feb. 28, 2014 for Japanese Patent Application No. 2011-508705.
Japanese Office Action dated Jul. 30, 2013 for Japanese Patent Application No. 2011-508705.
Cardio Medical Solutions, Inc. brochure titled: "Baladi Inverter for Clamp less Surgery"—Undated.
The problem: Closing wounds in deep areas during laparoscopic operations The solution: REMA Medizintechnik GmbH (no date).
European Exam Report re EP Application No. 09 743 752.9, dated Feb. 25, 2019.

\* cited by examiner

SUTURING DEVICES AND METHODS FOR SUTURING AN ANATOMIC VALVE

CROSS-REFERENCE TO RELATED APPLICATIONS

Any and all applications for which a foreign or domestic priority claim is identified in the Application Data Sheet as filed with the present application, are hereby incorporated by reference in their entirety under 37 CFR 1.57.

TECHNICAL FIELD

Embodiments of the present inventions relate to suturing devices and methods. Some embodiments of the present invention relate to suturing devices and methods for suturing an anatomic valve, for example, a heart valve such as a mitral valve, an aortic valve, a tricuspid valve, or a pulmonary valve.

BACKGROUND

Health practitioners frequently use sutures to close various openings such as cuts, punctures, and incisions in various places in the human body. Generally, sutures are convenient to use and function properly to hold openings in biological tissue closed thereby aiding in blood clotting, healing, and prevention of scaring.

SUMMARY OF THE DISCLOSURE

There are some circumstances under which it is not feasible to use conventional sutures and suturing methods to close an opening. Additionally, there are some circumstance under which the use of conventional sutures and suturing methods require invasive procedures that subject a patient to risk of infection, delays in recovery, increases in pain, and other complications.

Some heart valves may be weakened or stretched, or may have other structural defects, such as congenital defects, that cause them to close improperly, which can lead to blood flow contrary to the normal flow direction. This condition, referred to as regurgitation, incompetence, or insufficiency, can reduce blood flow in the normal direction. Regurgitation causes the heart to work harder to compensate for backflow of blood through these valves, which can lead to enlargement of the heart that reduces cardiac performance. While the tricuspid valve and the pulmonary valve may present these conditions, the mitral valve and aortic valve more frequently demonstrate these conditions.

A number of procedures have been developed to repair valves that do not close properly. Among these procedures is the Alfieri technique, sometimes called edge-to-edge repair, which involves suturing edges of the leaflets and pulling the leaflets closer together. In another technique, the chordae tendineae are replaced or shortened. A patch is sometimes applied to leaflets that have openings therein. In some instances, leaflets are reshaped by removing a section of the leaflet that is to be treated and the surrounding portion of the leaflet is sutured closed. Some valves are treated by attaching a ring around the outside of the malfunctioning valve. Other valves may be replaced with biological or mechanical replacements. These procedures are frequently performed by highly invasive procedures, which sometimes require opening a patient's chest, stopping the patient's heart and routing blood through a heart-lung machine. Robotically-assisted procedures have been employed to reduce the size of the openings required for such procedures.

Embodiments of suturing devices and methods for suturing biological tissue are disclosed herein. The suturing devices and their methods of use can be useful in a variety of procedures, such as treating (e.g., closing) wounds and naturally or surgically created apertures or passageways. For example, the suturing devices can be used to treat an anatomical valve, such as a heart valve, including heart valves that may be weakened or stretched, or have other structural defects, such as congenital defects, that cause them to close improperly. In some embodiments, one or more suturing devices can be used to treat or repair valves, such as the tricuspid, pulmonary, mitral, and aortic valves, for example. In some embodiments, one or more suturing devices can be used to perform procedures such as the Alfieri technique (edge-to-edge repair), replacement of the chordae tendineae, shortening of the chordae tendineae, patch application, leaflet reshaping, and attachment of prosthetics, such as rings and biological or mechanical replacement valves, for example.

In some embodiments, the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture pledget within the body.

In some embodiments, a device for suturing an anatomic valve comprises an elongate body, a needle, an arm, and a recess positioned between the elongate body and the arm. The needle can be operatively coupled to the elongate body for movement between a retracted position and an advanced position. The arm can be attached to the elongate body near a distal end of the elongate body for movement between a retracted position and an extended position. The arm can comprise a suture mount that is configured to releasably retain a suture portion. The suture mount can be positioned on the arm such that the needle retrieves the suture portion retained in the suture mount when the needle is moved from the retracted position to the advanced position and returned to the retracted position. The recess can be sized and shaped to receive a leaflet of a valve between the elongate body and the arm without damaging the leaflet.

In some embodiments, an anatomic valve can be sutured A suturing device comprising an elongate body can be positioned at least partially within the anatomic valve. A first arm can be deployed from the elongate body with the first arm releasably holding a first suture portion. The first arm can be at least partially closed about a first leaflet of the anatomic valve. While the first arm is at least partially closed about the first leaflet, a first needle can be advanced through the first leaflet to engage the first suture portion. The first suture portion can be drawn through the first leaflet. A second suture portion can be passed through a second leaflet. The first and second suture portions can be secured together.

In some embodiments, a heart valve can be sutured. A first elongate member can be advanced to a heart valve. A first arm can be extended from the elongate member around a first heart valve portion with the first arm releasably holding a first suture portion. A first needle can be advanced from the elongate member through a first heart valve portion to retrieve a first suture portion from the first arm. A second arm can be extended around a second heart valve portion with the second arm releasably holding a second suture portion. A second needle can be advanced through a second heart valve portion to retrieve the second suture portion from the second arm. The first and second suture portions can be secured to each other.

In some embodiments, the anatomic valve can be sutured using a single device, while in other embodiments the anatomic valve can be sutured using multiple devices. In embodiments using multiple devices, any two devices can be introduced to the treatments site using the same access or different accesses.

The disclosure describes examples of some embodiments of the inventions. The designs, figures, and description are non-limiting examples of some embodiments of the inventions. Other embodiments of the devices and methods may or may not include the features disclosed herein. Moreover, disclosed advantages and benefits may apply to only some embodiments of the inventions, and should not be used to limit the inventions.

BRIEF DESCRIPTION OF THE DRAWINGS

The above-mentioned and other features disclosed herein are described below with reference to the drawings of specific embodiments. The illustrated embodiments are intended for illustration, but not limitation. The drawings contain the following figures.

DETAILED DESCRIPTION OF SPECIFIC EMBODIMENTS

Embodiments of suturing devices and methods for suturing biological tissue are disclosed herein. The suturing devices and their methods of use can be useful in a variety of procedures, such as treating (e.g., closing) wounds and naturally or surgically created apertures or passageways. For example, the suturing devices can be used to treat an anatomical valve, such as a heart valve, including heart valves that may be weakened or stretched, or have other structural defects, such as congenital defects, that cause them to close improperly. In some embodiments, one or more suturing devices can be used to treat or repair valves, such as the tricuspid, pulmonary, mitral, and aortic valves, for example. In some embodiments, one or more suturing devices can be used to perform procedures such as the Alfieri technique (edge-to-edge repair), replacement of the chordae tendineae, shortening of the chordae tendineae, patch application, leaflet reshaping, and attachment of prosthetics, such as rings and biological or mechanical replacement valves, for example.

In some embodiments, the suturing devices can be used to close or reduce a variety of other tissue openings, lumens, hollow organs or natural or surgically created passageways in the body. In some embodiments, the suturing devices can be used to suture prosthetics, synthetic materials, or implantable devices in the body. For example, the devices can be used to suture pledget within the body.

Figure 1:
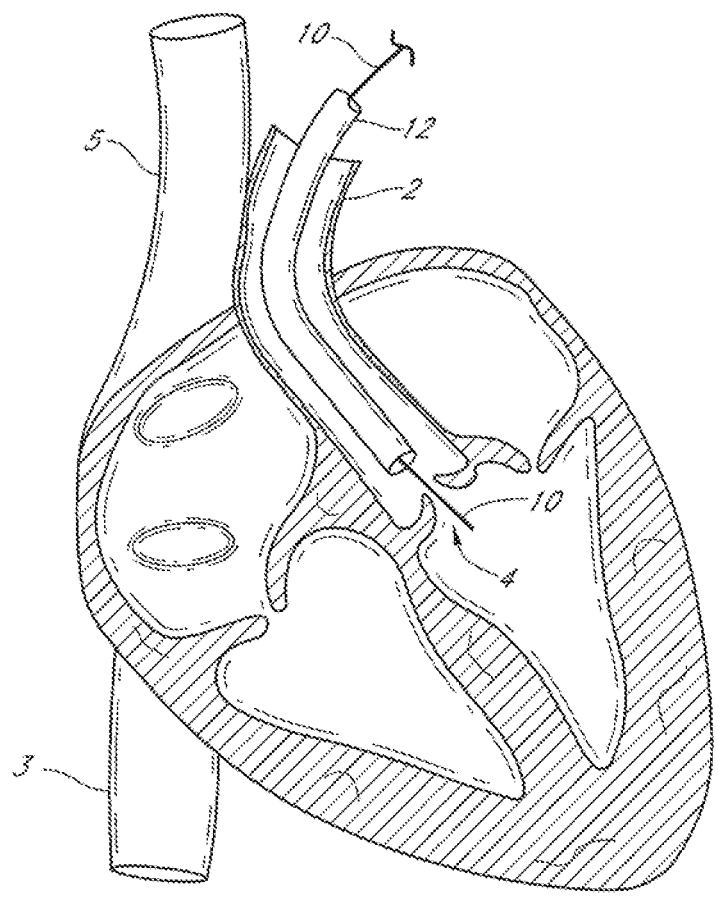
FIG. 1 illustrates a method of providing access to an exemplifying use environment, such as an aortic valve of a heart.

FIG. 1 illustrates an exemplifying use environment for suturing an aortic valve 4. Adaption of the devices and methods disclosed herein for suturing a heart valve may also be made with respect to procedures for suturing other bodily tissue and procedures for suturing prosthetics, synthetic materials, or implantable devices in the body. As depicted by FIG. 1, a guidewire 10 can be advanced through the aorta 2 to a position at or near the aortic valve 4. The guidewire 10 can be advanced into the aorta 2 through a subclavian artery (not shown). It is anticipated that the heart may be accessed through any of a variety of pathways. For example, the heart may be accessed through the inferior vena cava 3, the superior vena cava 5, or other vascular access. With the guidewire 10 in place, the physician can insert a sheath 12 to a position at or near the aortic valve 4. This sheath 12 is typically a single lumen catheter with a valve on its proximal end. The valve can be used, for example, to prevent extraneous bleed back or to introduce medication into the patient's body. A suturing device, such as those described further below, can then be advanced through the lumen of the sheath 12. In an alternative embodiment, the suturing device can be advanced over the guidewire 10 and positioned at or near the aortic valve 4 without the need to insert an introducer sheath 12.

Figure 2:
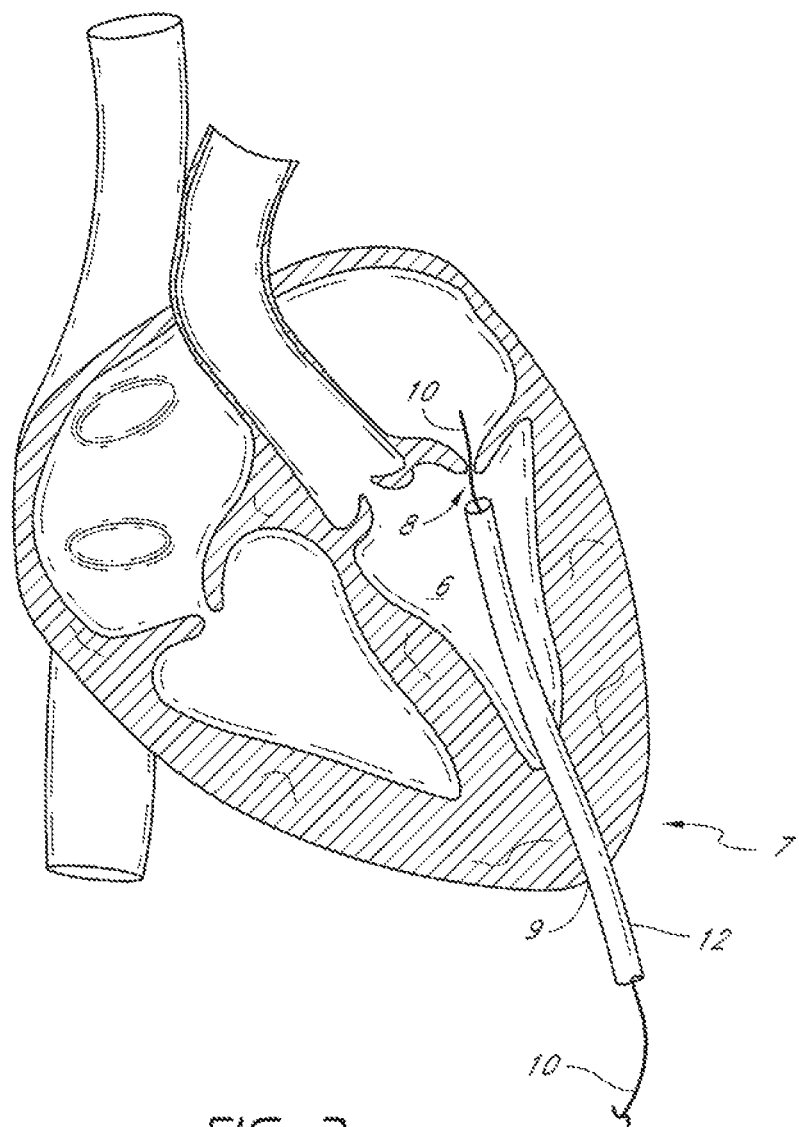
FIG. 2 illustrates a method of providing access to an exemplifying use environment, such as a mitral valve of a heart.

FIG. 2 illustrates another exemplifying use environment for suturing a mitral valve 8. As depicted by FIG. 2, a guidewire 10 is advanced into the left ventricle 6 of the heart through a puncture or incision 9 near an apex 7 of the left ventricle 6. The heart may be accessed through a limited thoracotomy, small trocar puncture, or small catheter puncture. Other access paths may be used. The guidewire 10 can then be further positioned at or near the mitral valve 8. With the guidewire 10 in place, the physician can insert a sheath 12 to the left ventricle 6. The sheath 12 can be placed at or near the mitral valve 8. The suturing device can then be advanced through the lumen of the sheath 12. In an alternative embodiment, the suturing device can be advanced over the guidewire 10 and positioned at or near the mitral valve 8 without the need to insert an introducer sheath 12.

FIGS. 3-9 illustrate an embodiment of a suturing device 100 that can be used to suture an anatomical valve, such as a heart valve. While the device 100 will be described with reference to suturing an anatomical valve, such as a heart valve, the device 100 could be used to suture other biological tissue and implantable devices and materials. The suturing device 100 can comprise a distal assembly 102, one or more suture clasp arms 104, and one or more suture catch mechanisms 106. The suturing device 100 can further comprise an elongate member (not shown) to facilitate manipulation of the suture clasp arm(s) 104 and the suture catch mechanism(s) 106 from a remote location. For example, the elongate member can comprise one or more lumens to accommodate a length of suture, or one or more actuator rods for manipulating the suture clasp arm(s) 104 and the suture catch mechanism(s) 106, or both. In some embodiments, the distal assembly 102 can comprise a portion of the elongate member.

Figure 6:
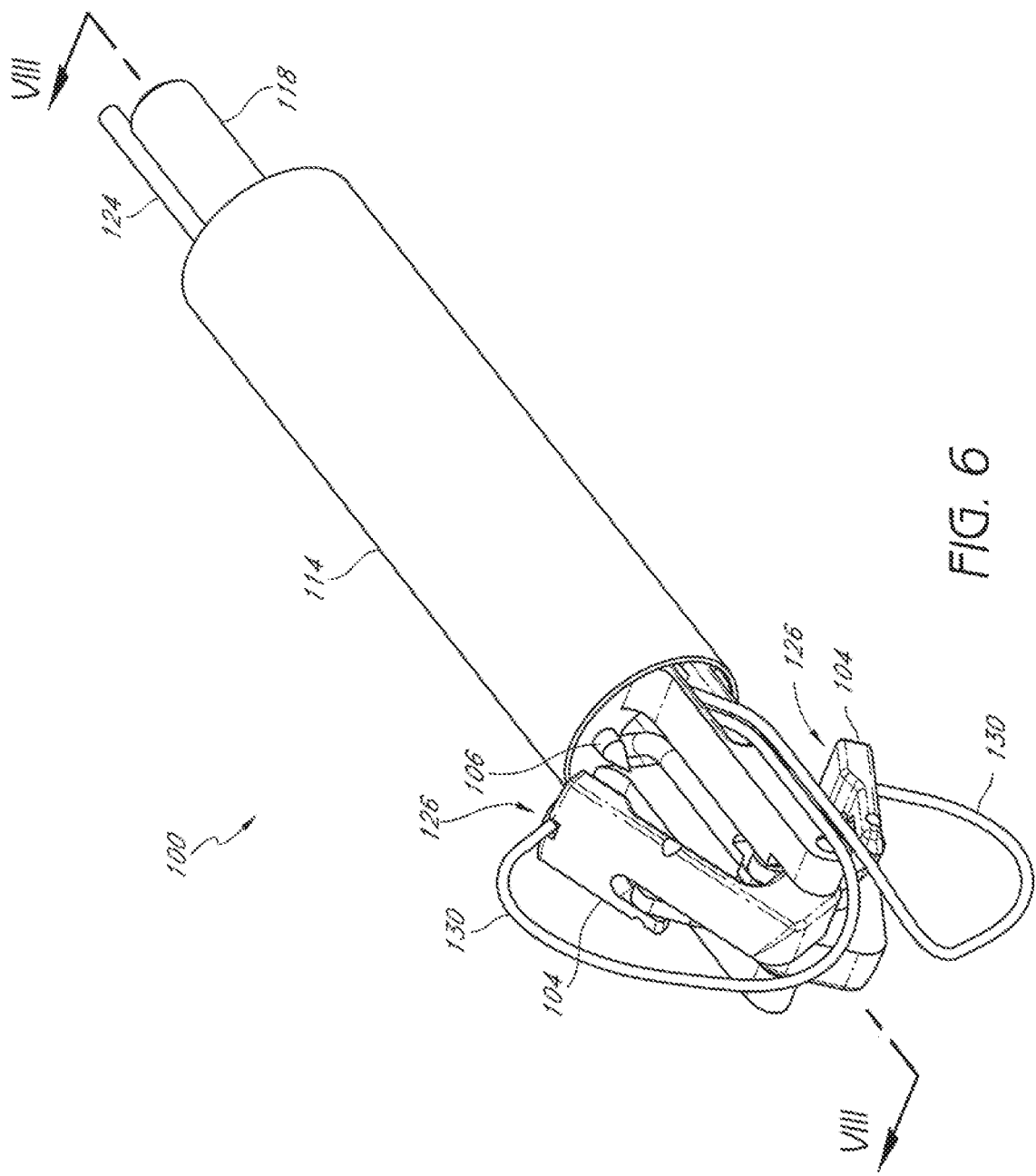
FIG. 6 is a perspective view of the embodiment of FIG. 3, as in FIG. 5, showing a casing attached to the device.

The distal assembly 102 can comprise a proximal mount 108, distal mount 110, a hub 112, and a casing 114 (FIG. 6). The proximal mount 108 can be fixedly connected to the distal mount 110 by the casing 114. The hub 112 can be positioned within the casing 114 for sliding movement between the proximal mount 108 and the distal mount 110.

Figure 5:
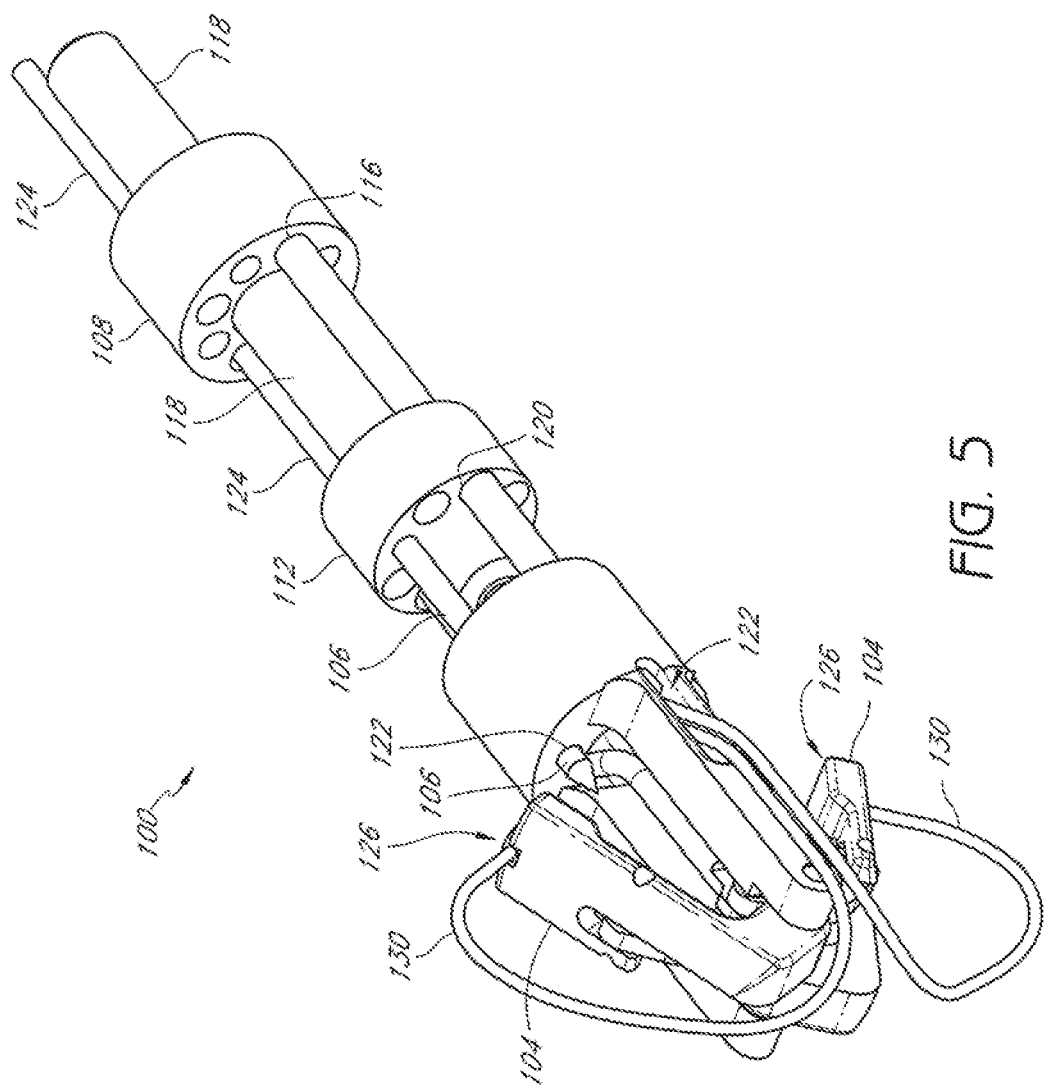
FIG. 5 is a perspective view of the embodiment of FIG. 3, with the suture clasp arms in an extended position and the suture catch mechanisms in a partially advanced position.

The proximal mount 108 can be connected to the elongate member (not shown). Alternatively, a distal end of the elongate member can form or be integrally formed with the proximal mount 108. In some embodiments, the elongate member can comprise the casing 114. The proximal mount 108 can comprise one or more lumens 116, as shown in FIGS. 3 and 5.

The hub 112 can be fixedly connected to the suture catch mechanism(s) 106 and an actuator rod 118. The actuator rod 118 can move through a lumen 116 in the proximal mount 108. Accordingly, distal advancement of the actuator rod 118 causes distal advancement of the suture catch mechanism(s) 106. The hub 112 can comprise one or more lumens 120.

Figure 3:
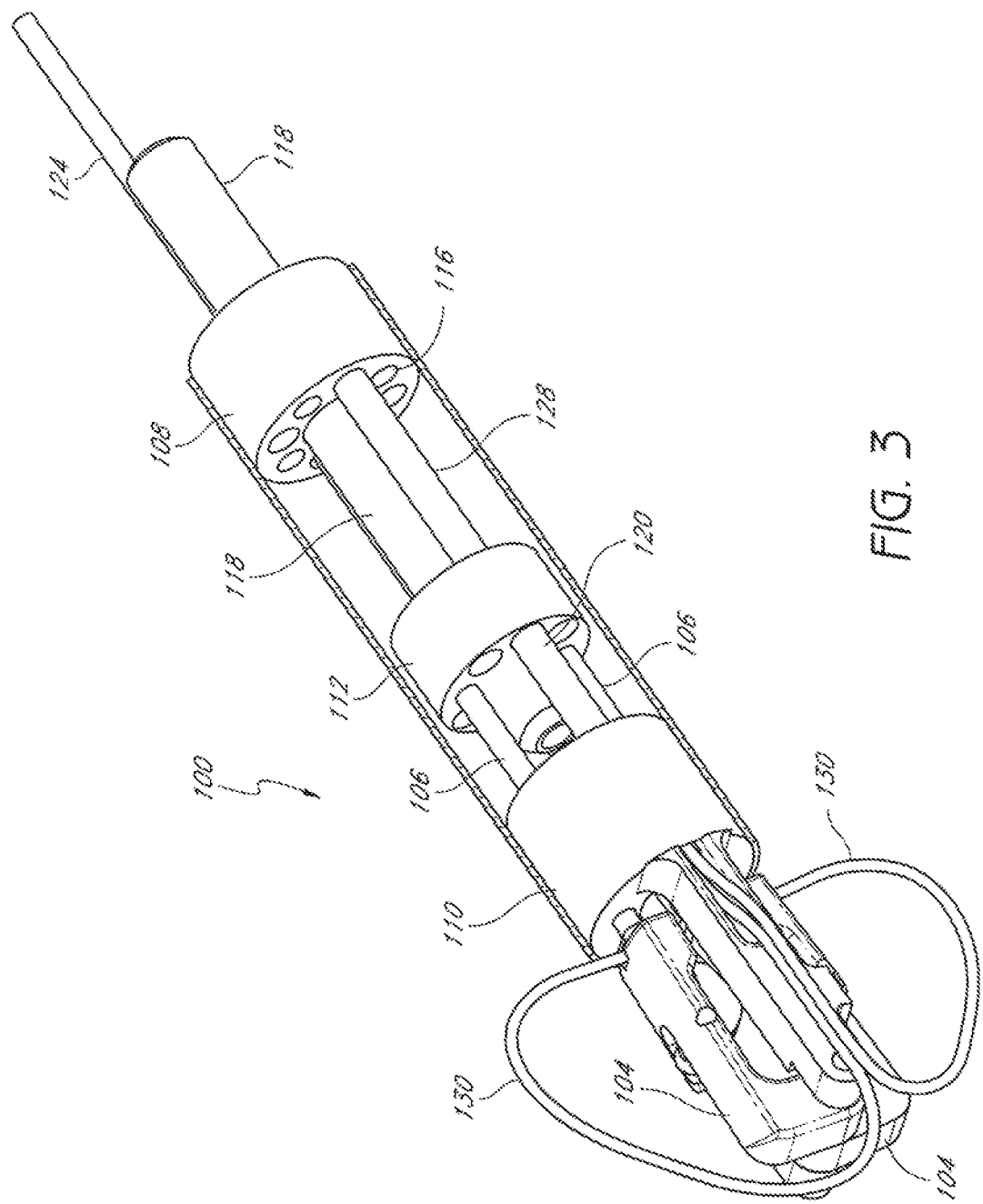
FIG. 3 is a perspective view of an embodiment of a suturing device with suture clasp arms in a retracted position and a casing shown in cross-section.
Figure 4:
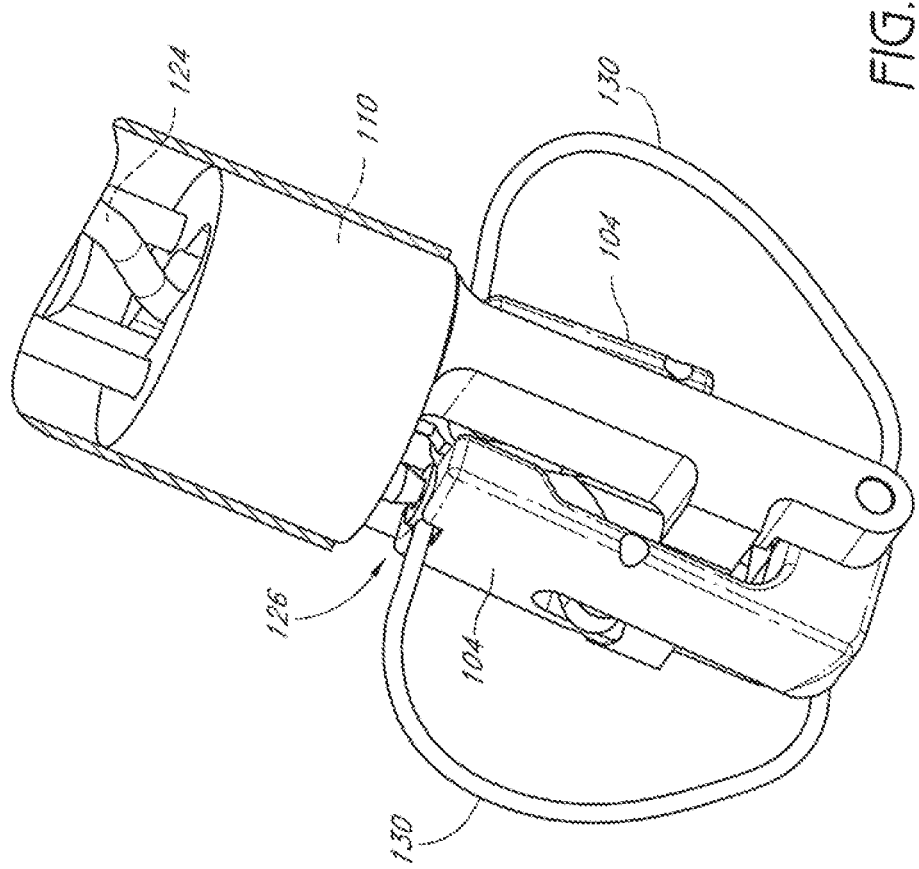
FIG. 4 is an enlarged perspective view of the embodiment of FIG. 3 with the casing shown in cross-section, showing suture catch mechanisms in a partially advanced position.

The suture clasp arm(s) 104 can be pivotally connected to the distal mount 110 such that the suture clasp arm(s) 104 can move between a retracted position, illustrated in FIGS. 3-4, and an extended position, illustrated in FIGS. 5-7A. Although the arms 104 of the device 100 that is illustrated in FIGS. 3-9 pivot about a distal end of the arms 104, the arms 104 can pivot about a proximal end of the arms 104 in other embodiments.

The suture clasp arm(s) 104 can be connected to an actuator rod 124, which can move through a lumen 116 in the proximal mount 108. The arm(s) 104, the distal mount 110, and the rod 124 can be connected such that distal movement of the rod 124 causes the arm(s) 104 extend and proximal movement of the rod 124 causes the arm(s) 104 to retract. In some embodiments, the arm(s) 104 can extend to a position that is substantially perpendicular to their fully-retracted position. In other embodiments, the arm(s) 104 can move less than 90° between the fully-retracted position and the fully-extended position.

The distal mount 110 can comprise one or more lumens 122 (FIG. 5) to allow movement of the suture catch mechanism(s) 106 through the distal mount 110. Additionally or alternatively, the one or more lumens 122 can accommodate a length of suture, the actuator rod 124, or both.

The suture clasp arm(s) 104 can have suture clasps 126 to releasably hold a suture portion 130. The suture catch mechanism(s) 106 can be advanced to engage the suture portion(s) 130 held by the suture clasp arms(s). Once the suture catch mechanism(s) 106 have engaged the suture end portion(s) 130, the suture catch mechanism(s) 106 can be retracted to pull the suture ends from the suture claps 126.

In some embodiments, the suture clasps 126 can be positioned on the suture clasp arm 104 such that the suture catch mechanism 106 retrieves the suture end portion 130 retained in the suture clasp 126 while the suture clasp arm 104 is at least partially retracted from its fully-extended position. In some embodiments, the suture clasps 126 can be positioned on the suture clasp arm 104 such that the suture catch mechanism 106 retrieves the suture end portion 130 retained in the suture clasp 126 while the suture clasp arm 104 is fully retracted. In some embodiments, the suture catch mechanism 106 can be advanced in a continuously longitudinal direction to engage the suture clasp 126 of the suture clasp arm 104 while the suture clasp arm is fully retracted. In some embodiments, the suture clasp 126 can be located on a proximally-facing side of a suture clasp arm 104 that pivots about a distal end of the suture clasp arm. In some embodiments, the suture clasp 126 can be located on a distally-facing side of a suture clasp arm 104 pivots about a proximal end of the suture clasp arm.

In some embodiments, the suture clasp arm 104 can be configured to receive a tissue-piercing portion of the corresponding suture catch mechanism 106. For example, in some embodiments, when the suture catch mechanism 106 is fully advanced, the tissue-piercing portion can be fully received with the corresponding suture clasp arm 104. In some embodiments, the suture clasp arm 104 can receive the tissue-piercing portion of the suture catch mechanism 106 when the arm is at least partially closed. In some embodiments, suture clasp arm 104 can receive the tissue-piercing portion of the suture catch mechanism 106 when the arm is fully retracted.

Figure 7A:
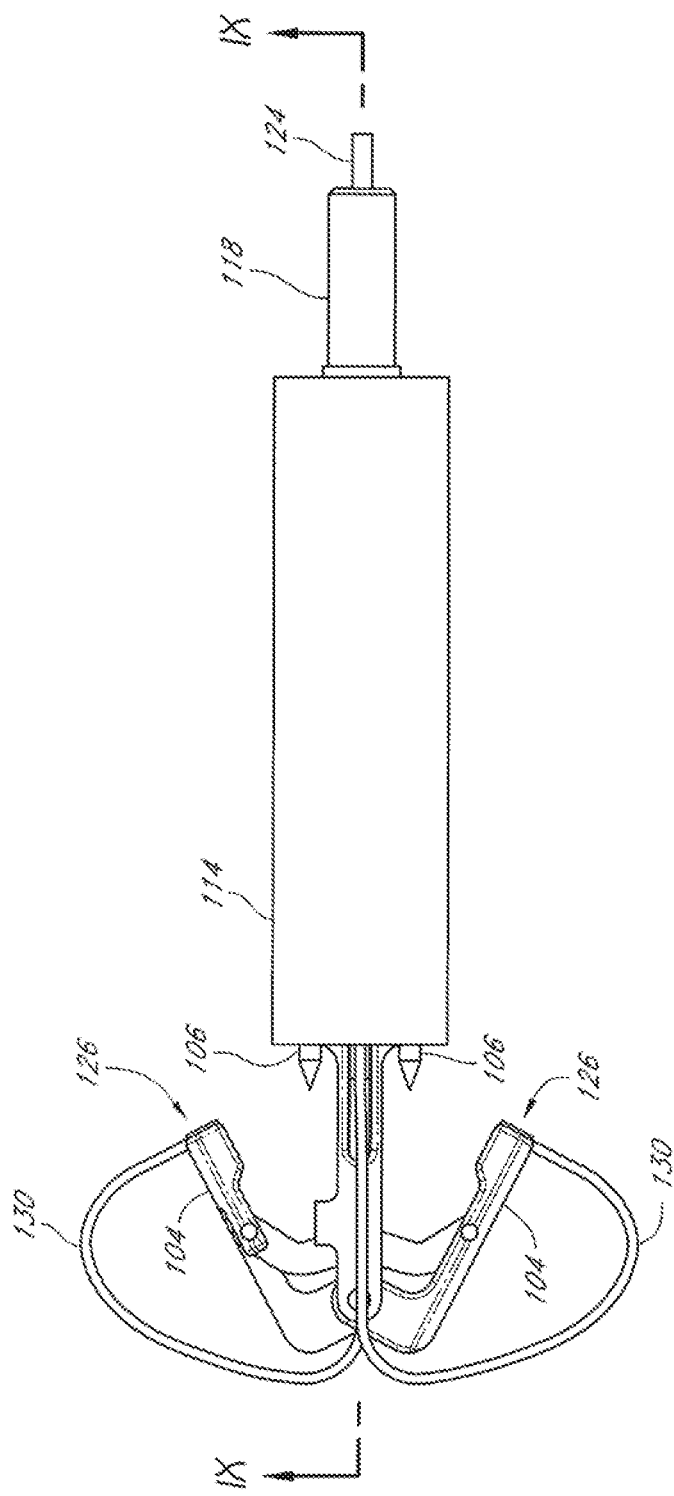
FIG. 7A is a plan view of the embodiment of FIG. 3, with the suture clasp arms in an extended position.
Figure 7B:
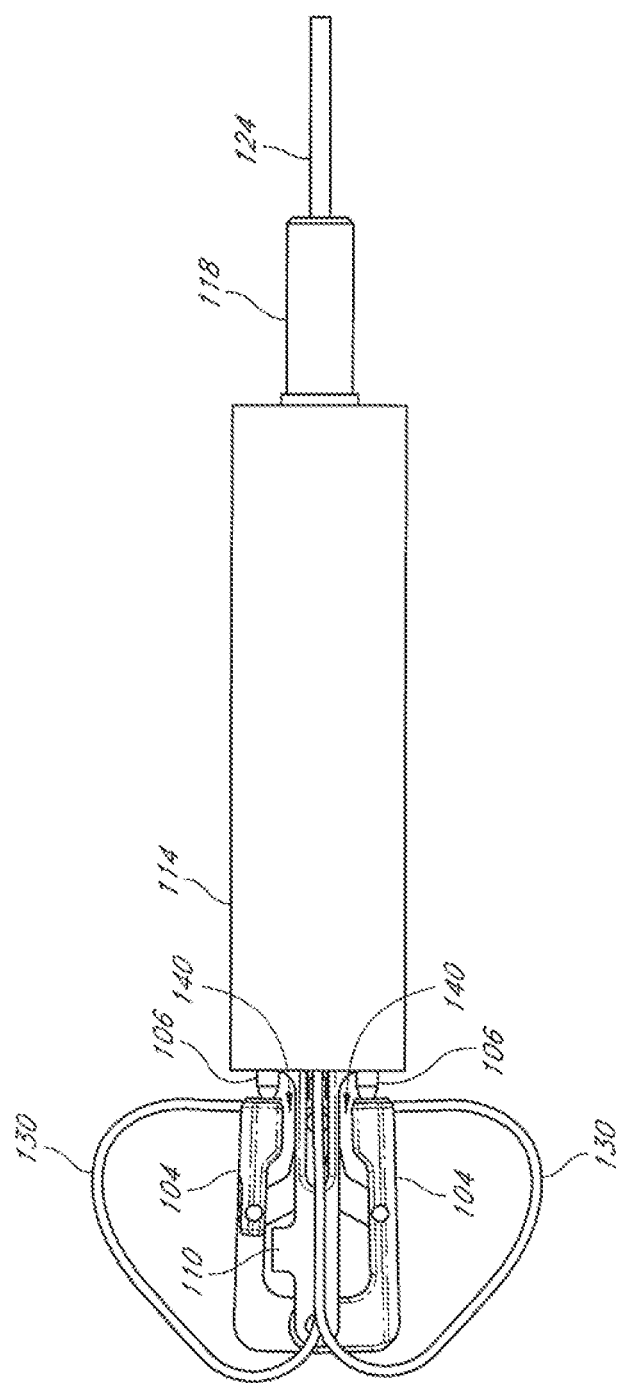
FIG. 7B is a plan view as in FIG. 7A, but with the suture clasp arms retracted.
Figure 8:
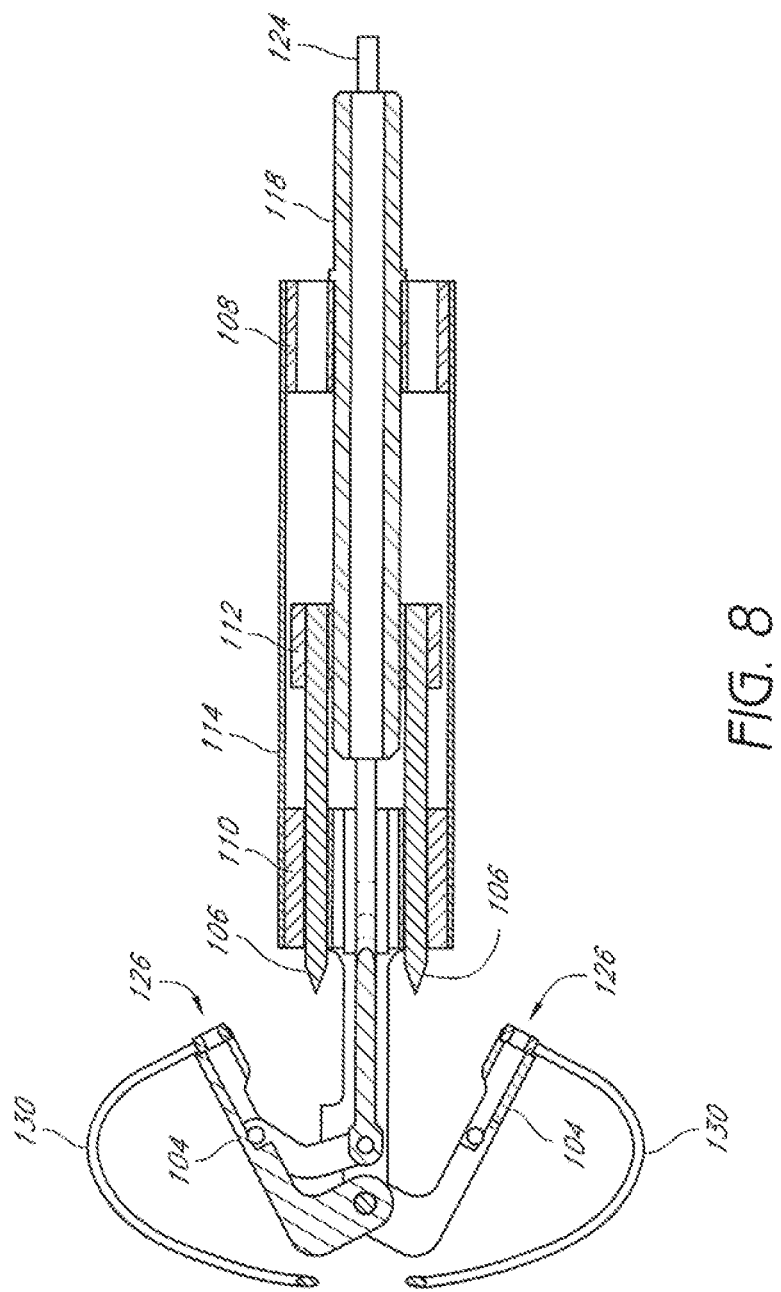
FIG. 8 is a cross-sectional view of the embodiment of FIG. 3, along a line VIII-VIII in FIG. 6.
Figure 9:
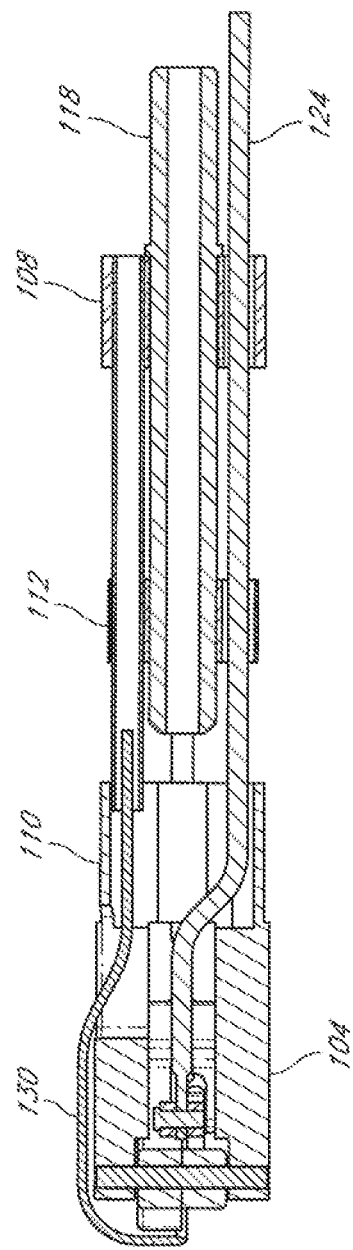
FIG. 9 is a cross-sectional view of the embodiment of FIG. 3, along a line IX-IX in FIG. 7A.

In some embodiments, the device 100 can comprise a recess 140 between the suture clasp arm 104 and the distal mount 110, or other component of the distal assembly 102, when the suture clasp arm 104 is fully retracted, as illustrated in FIG. 7B. In some embodiments, a tissue portion, such as a valve leaflet, can be received with the recess 140 with the suture clasp arm 104 fully retracted and without damaging the tissue portion. In some embodiments, the tissue portion can be held in the recess 140 by the suture clasp arm 104 while the suture clasp arm is fully retracted. In some embodiments, the tissue portion can be held in the recess 140 by the suture clasp arm 104 while the suture clasp arm is at least partially retracted.

In some embodiments, the recess 140 can have a size and shape to receive a leaflet of a valve between the elongate body and the arm when the arm is at least partially retracted without damaging the leaflet. In some embodiments, the recess 140 can have a size and shape to receive a leaflet of a valve between the elongate body and the arm when the arm is fully retracted without damaging the leaflet. In some embodiments, the recess 140 can have a size and shape to retain the leaflet between the elongate body and the arm when the arm is at least partially retracted without damaging the leaflet. In some embodiments, the recess 140 can have a size and shape to retain the leaflet between the elongate body and the arm when the arm is fully retracted without damaging the leaflet.

Figure 11:
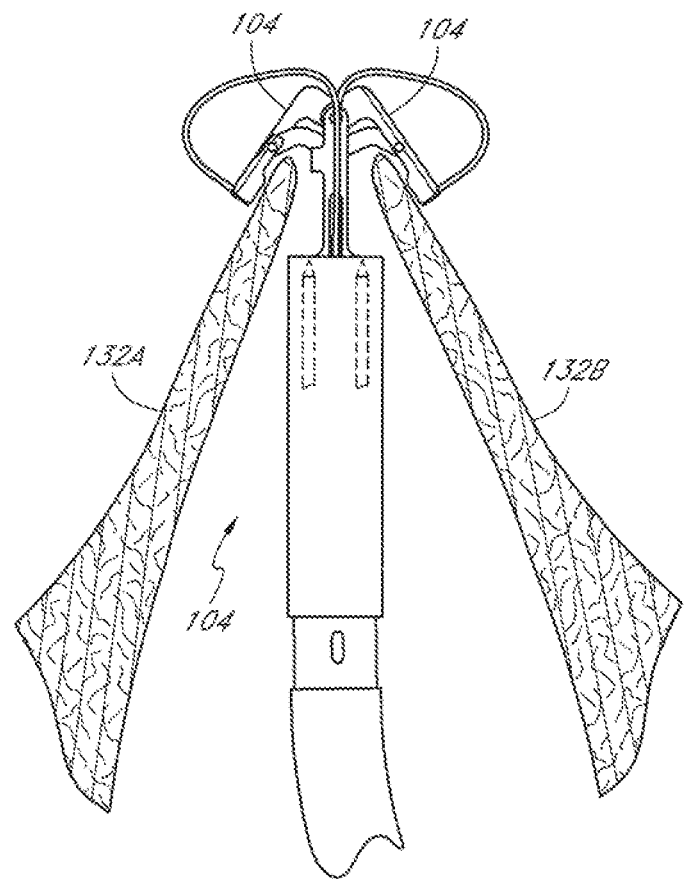
FIG. 11 is a schematic representation as in FIG. 10 with suture clasp arms positioned around first and second leaflets of the valve.

In some embodiments, the device 100 can be manipulated with the suture clasp arm(s) 104 in the extended position to place a tissue portion, such as a leaflet of a valve, between the suture clasp arm 104 and the distal mount 110, as shown, for example, in FIG. 11. In some embodiments, the suture clasp arm 104 can be at least partially closed about the tissue portion. In some embodiments, the suture clasp arm 104 can be fully closed about the tissue portion. In some embodiments, the suture clasp arm 104 can be at least partially retracted to securely hold the tissue portion between the suture clasp arm 104 and the distal mount 110. In some embodiments, the suture clasp arm 104 can be moved to the retracted position to securely hold the tissue portion between the suture clasp arm 104 and the distal mount 110, as shown, for example, in FIG. 12. In some embodiments, the tissue portion is not damaged by closing the suture clasp arm 104 about the issue portion or holding the tissue portion between the suture clasp arm 104 and the distal mount 110.

Figure 13:
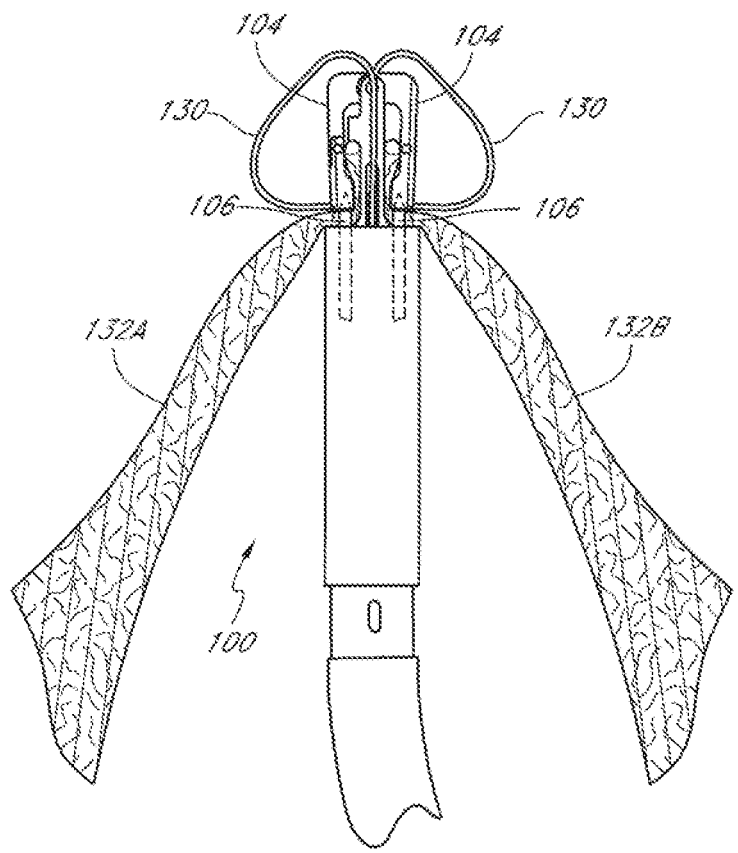
FIG. 13 is a schematic representation as in FIG. 12 showing suture catch mechanisms engaging the suture clasp arms.

With the tissue portion held between the arm 104 and the distal mount 110, the corresponding suture catch mechanism 106 can be advanced to engage the suture portion 130 held by the suture clasp 126 of the arm 104, as shown, for example, in FIG. 13. The suture portion 130 can then be drawn through the tissue portion by the suture catch mechanism 106, as shown, for example, in FIG. 14. In other embodiments, the suture catch mechanism(s) 106 can be advanced toward the suture clasp arm(s) 104 and retrieve the suture ends from the suture clasps 126 when the arm(s) 104 are in the extended position. In some embodiments, the suture catch mechanism can be a needle.

In some embodiments, the distal assembly 102 can comprise a tube or conduit 128 to accommodate a suture and prevent damage to the suture by any component of the device 100. In some embodiments, the conduit 128 extends through a lumen 116 in the proximal mount 108, a lumen 120 in the distal mount 110, and a lumen 122 in the hub 112.

Further details regarding devices, structures, and methods that may be incorporated with the above embodiments are provided in U.S. Pat. No. 7,090,686 and U.S. Patent Application Publication No. 2008/0269786, published on Oct. 30, 2008, the entireties of all of which are hereby incorporated by reference herein and form a part of this specification. For example, in some embodiments having plural arms 106 and plural suture catch mechanisms 106, each arm 104 and each suture catch mechanism 106 of the device 100 can be independently actuated to move individually between the retracted position and the extended position.

Figure 10:
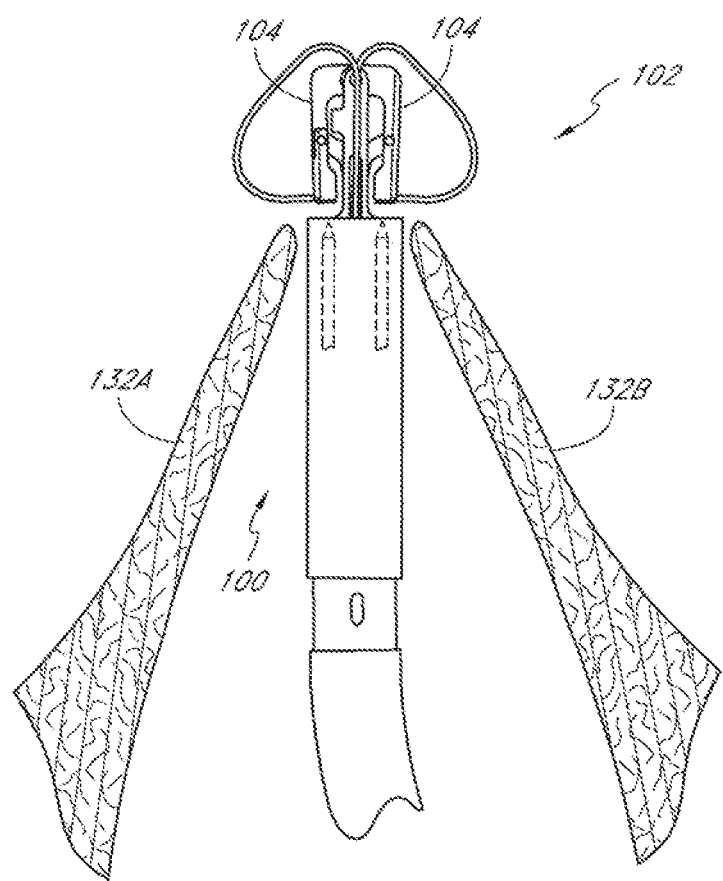
FIG. 10 is a schematic representation an embodiment of a suturing device positioned in a passage through a valve.

FIGS. 10-15 illustrate a method for suturing an anatomical valve according to one embodiment. The distal end of a suturing device 100 can be positioned between leaflets 132 of a valve, as shown in FIG. 10. The device 100 can be advanced through the vasculature to the desired position. For example, the device 100 can be advanced through the inferior vena cava into right atrium and through the septum and positioned in the passage through the mitral valve 8 (FIG. 2).

The suturing device 100 can be advanced to allow suture clasp arms 104 to extend from the distal assembly 102. The suture clasp arms 104 can then be extended and the device 100 can be retracted until the suture clasp arms 104 extend around a first leaflet 132A and a second leaflet 132B of the valve, as shown in FIG. 11.

Figure 12:
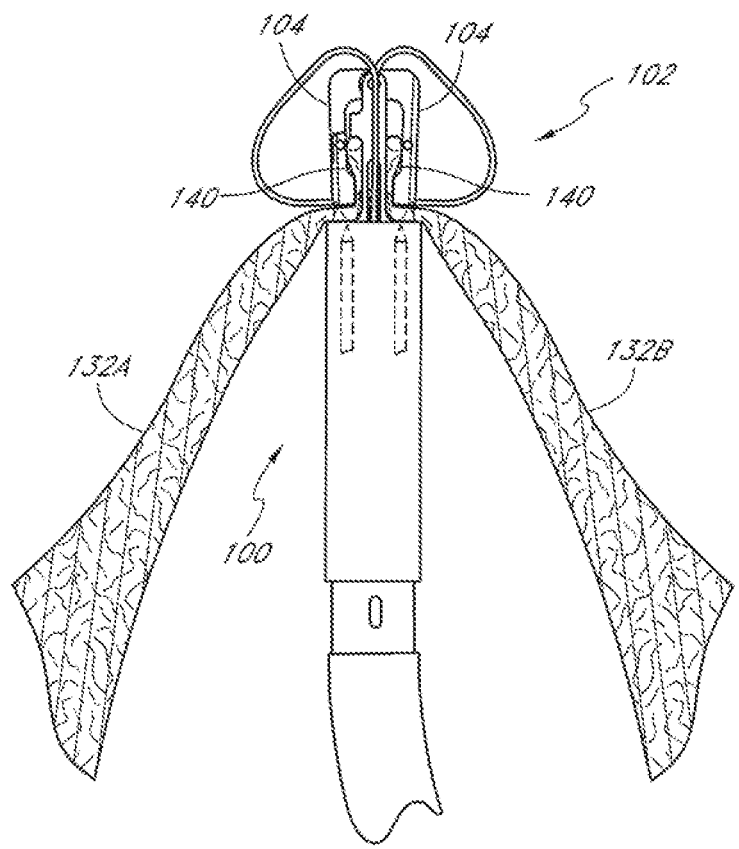
FIG. 12 is a schematic representation as in FIG. 11 with suture clasp arms retracted.

Once the suture clasp arms 104 have been properly positioned around the first and second leaflets 132, the suture clasp arms 104 can be retracted to trap portions of the first and second leaflets 132, for example between the suture clasp arms 104 and the distal mount 110 in the recess 140, as illustrated in FIG. 12.

With the first and second leaflets 132 trapped the suture catch mechanisms 106 can be advanced from the distal assembly 102 to penetrate the first and second leaflets 132 and engage the suture portions 130 held by the suture clasp arms 104, as illustrated in FIG. 13.

Figure 14:
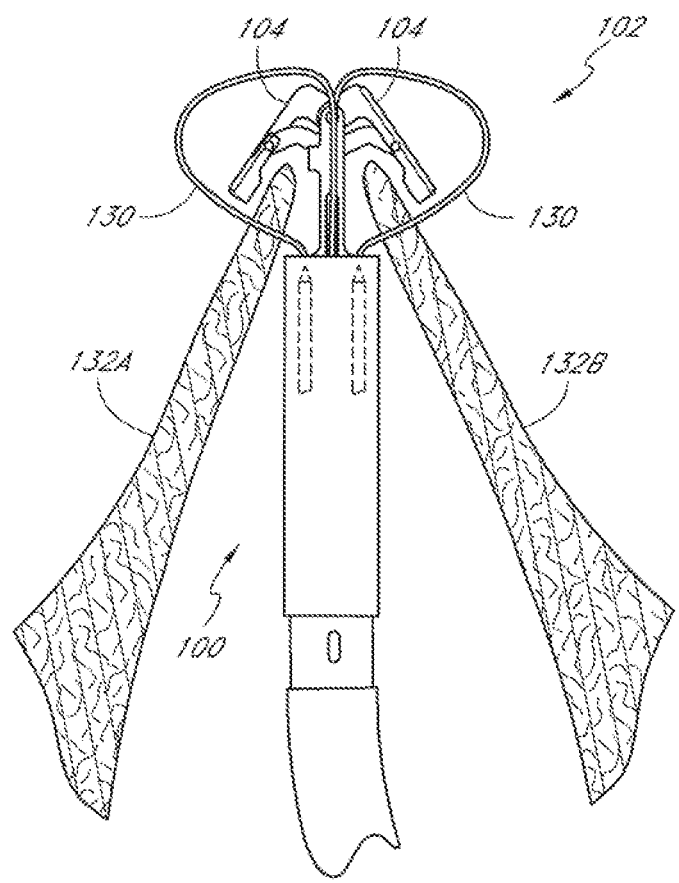
FIG. 14 is a schematic representation as in FIG. 13 showing the suture catch mechanisms and suture portions retracted through the first and second leaflets.

After the suture portions 130 has been engaged, the suture catch mechanisms 106 and engaged suture portions 130 are then retracted through the tissue of the first and second leaflets 132 into the distal assembly 102, as shown in FIG. 14. The suture clasp arms 104 can be extended to release the first and second leaflets 132. After the first and second leaflets have been released, the device 100 can be advanced slightly so that the suture clasp arm 104 can be moved to the retracted position without pinching the leaflets 132. The first suturing device 100 can then be withdrawn from the valve.

Figure 15:
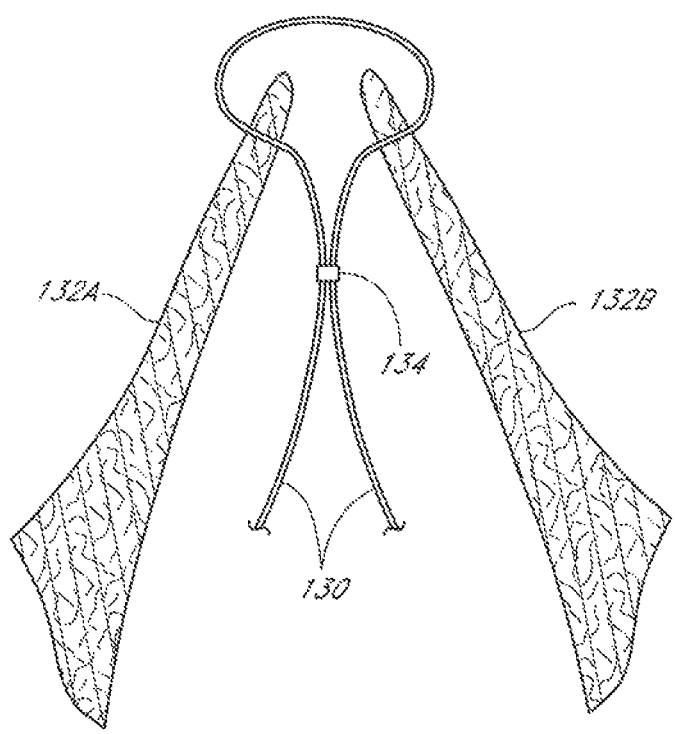
FIG. 15 is a schematic representation as in FIG. 14 showing the suture portions extending through the first and second leaflets and being joined by a knot.

As shown in FIG. 15, after the suturing device 100 has been withdrawn, the suture portions 130 extend from the leaflets 132. The suture portions 130 can be pulled to draw the first leaflet 132A and the second leaflet 132B towards one another. The suture portions 130 can then be secured together to limit movement of the leaflets 132A, 132B relative to one another, as illustrated in FIG. 15 for example. In some embodiments, the sutures 130 can hold a portion of the leaflets 132A, 132B in contact with one another. In other embodiments, the sutures 130 merely hold the leaflets 132A, 132B in closer proximity to one another than they had previously been. The suture portions 130 can be secured together by tying a knot 134 according to any known method or by applying a knot 134, such as described in U.S. Patent Publication No. 2007/0010829 A1, published Jan. 11, 2007, the entirety of which is hereby incorporated herein by reference. The suture portions 130 can be secured together exterior to the body or within the body. Any excess portion of sutures 130 can be trimmed.

Figure 16:
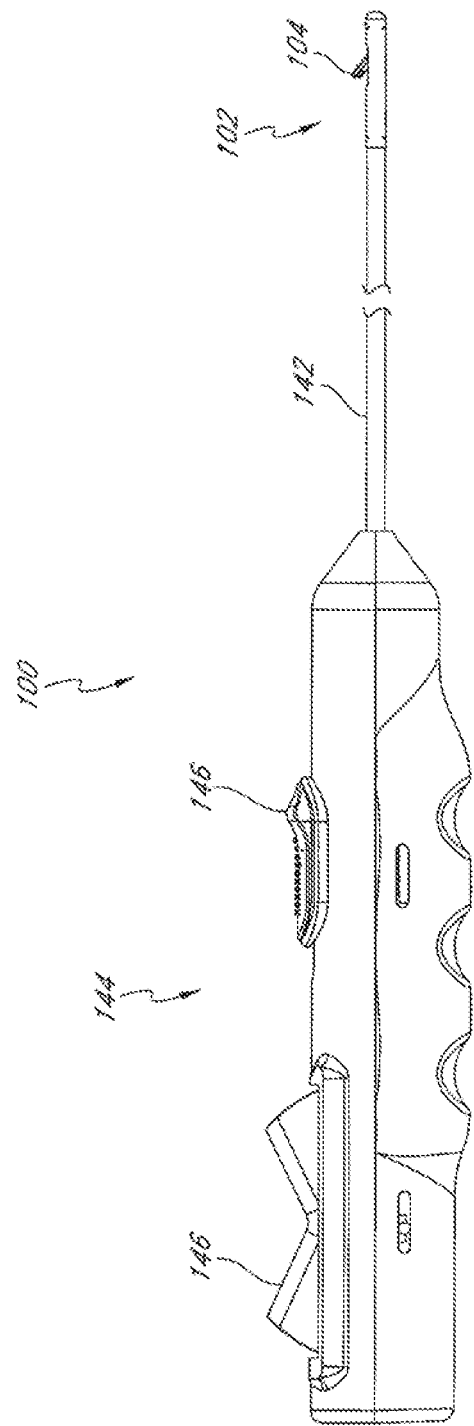
FIG. 16 is a plan view of an embodiment of a suturing device with a suture clasp arm in an extended position.
Figure 17:
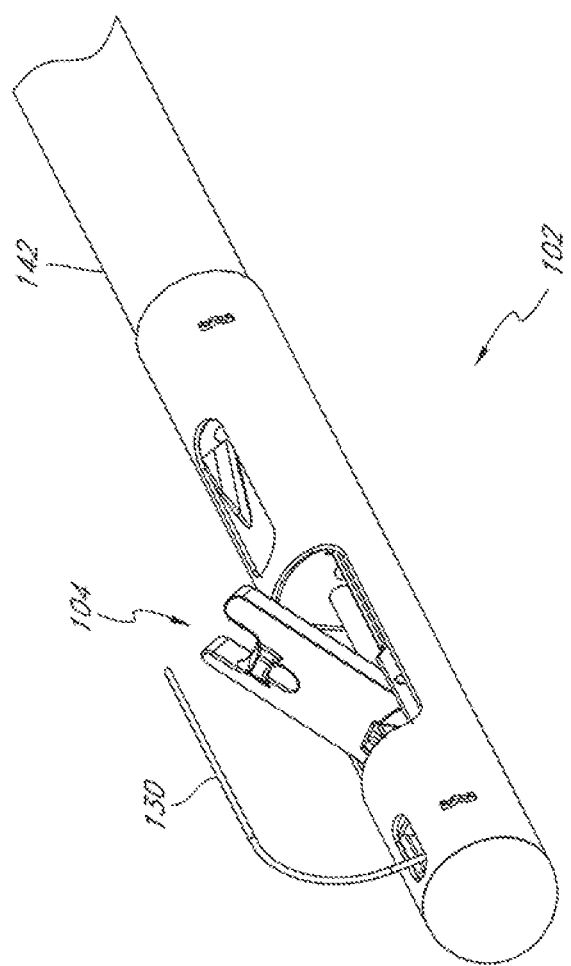
FIG. 17 is an enlarged perspective view of the distal end of the suturing device of FIG. 16 with the suture clasp arm in an extended position.

FIGS. 16 and 17 illustrate an embodiment of a suturing device 100 that can be used to suture an anatomical valve, such as a heart valve. The suturing device 100 can comprise a distal assembly 102, a single suture clasp arm 104, and a single suture catch mechanism 106.

As illustrated in FIGS. 16 and 17, the suturing device 100 can comprise an elongate member 142 to facilitate manipulation of the suture clasp arm 104 and the suture catch mechanism 106 from a remote location. For example, the elongate member can comprise one or more lumens to accommodate a length of suture, or one or more actuator rods for manipulating the suture clasp arm 104 and the suture catch mechanism 106, or both. The suturing device 100 can comprise a handle 144 with one or more actuators and/or pulls 146 for moving the suture clasp arm 104 and the suture catch mechanism 106. Further details regarding handles and associated components, including actuator rods, are provided in U.S. Patent Application Publication No. 2008/0269786, published on Oct. 30, 2008, the entirety of which is hereby incorporated by reference herein and forms a part of this specification.

In some embodiments, the suture clasp arm 104 can pivot about an axis located at a distal end of the suture clasp arm 104 when the suture clasp arm 104 is in a retracted position, as illustrated in FIGS. 16 and 17.

FIGS. 18-26 illustrate a method according to one embodiment for suturing an anatomical valve. Although the illustrated method involves two devices 100, each having a single suture clasp arm 104 and a single suture catch mechanism 106, the illustrated method can also be practiced using a single suturing device 100 having more than one arm 104 and more than one suture catch mechanism 106.

Figure 18:
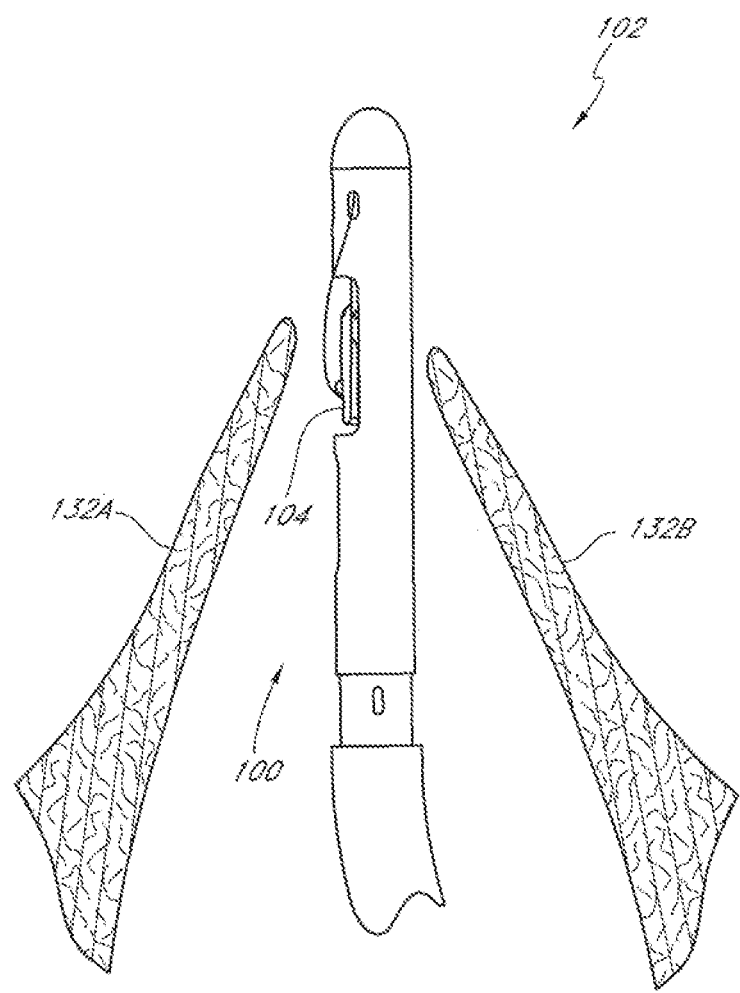
FIG. 18 is a schematic representation an embodiment of a first suturing device positioned in a passage through a valve.

The distal end of a first suturing device 100 can be positioned between leaflets 132 of a valve, as shown in FIG. 18. The device 100 can be advanced through the vasculature to the desired position. For example, the device 100 can be advanced through the inferior vena cava into right atrium and through the septum and positioned in the passage through the mitral valve 8 (FIG. 2).

Figure 19:
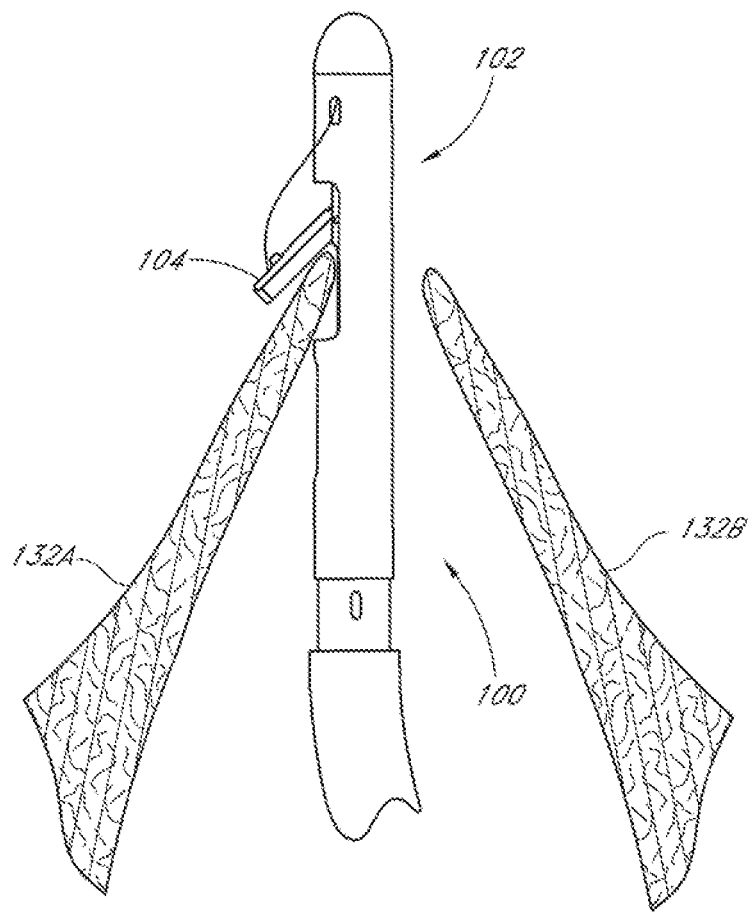
FIG. 19 is a schematic representation as in FIG. 18 with a suture clasp arm positioned around a first leaflet of the valve.

The suturing device 100 can be advanced to allow a suture clasp arm 104 to extend from the distal assembly 102. The suture clasp arm 104 can then be extended and the device 100 can be retracted until the suture clasp arm 104 extends around a first leaflet 132A of the valve, as shown in FIG. 19.

Figure 20:
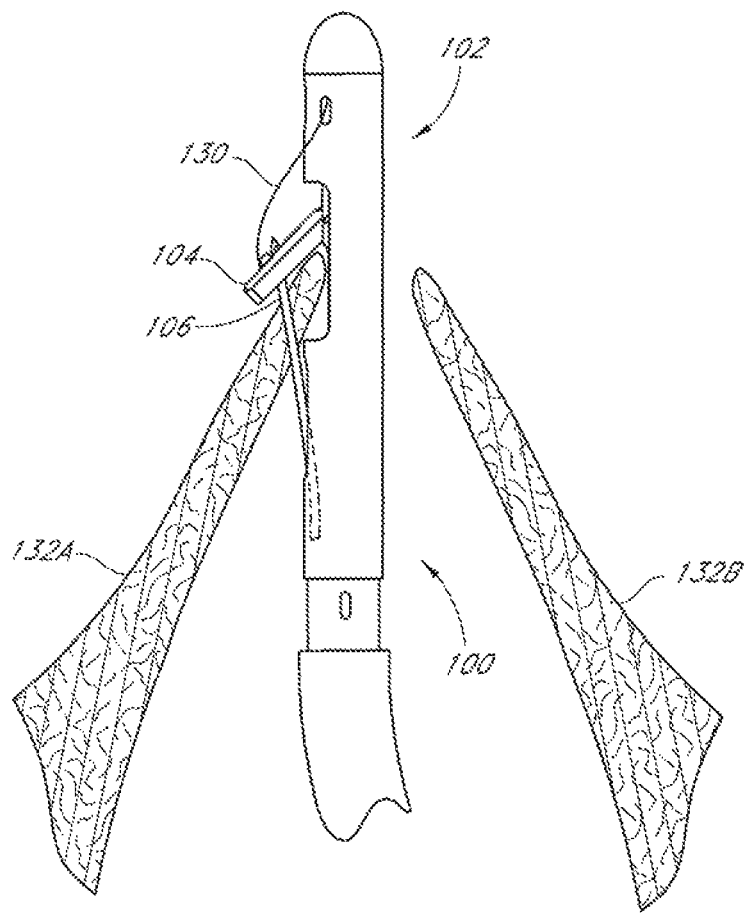
FIG. 20 is a schematic representation as in FIG. 19 showing a suture catch mechanism engaging the suture clasp arm.

Once the suture clasp arm 104 has been properly positioned around the first leaflet 132A, the suture catch mechanism 106 can be advanced from the distal assembly 102 to penetrate the first leaflet 132A and engage the suture portion 130 held by the suture clasp arm 104, as illustrated in FIG. 20. In some embodiments, the suture clasp arm 104 can be moved to the retracted position to securely hold a portion of the first leaflet 132A between the arm 104 and the distal mount 100 in the recess 140, for example, before the suture catch mechanism 106 is advanced through the first leaflet 132A to engage the suture end, as described above.

Figure 21:
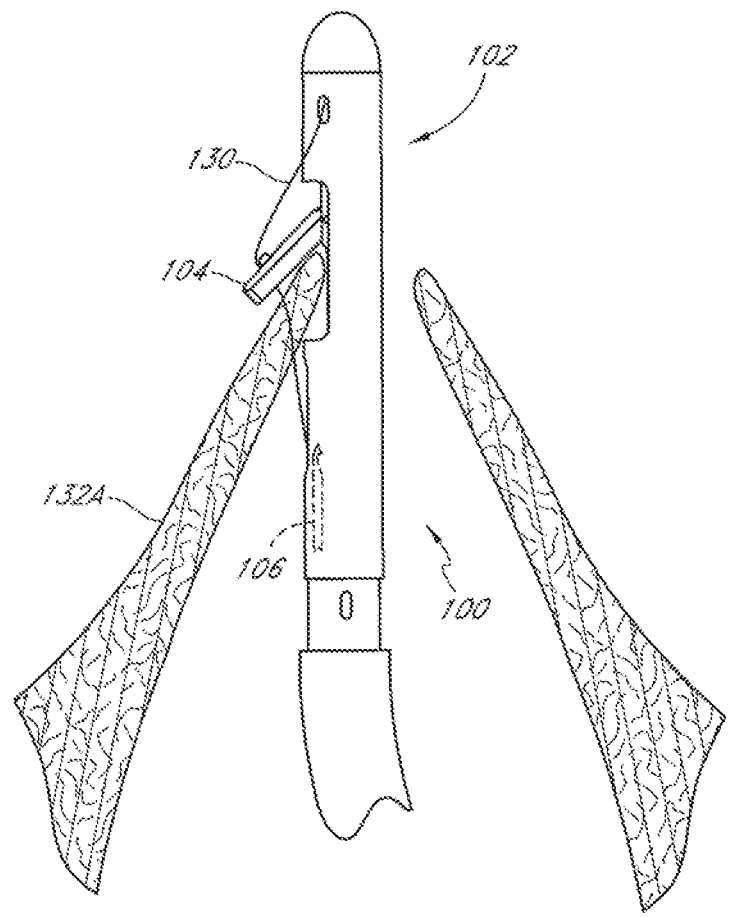
FIG. 21 is a schematic representation as in FIG. 20 showing the suture catch mechanism and a suture portion retracted through the first leaflet.

After the suture portion 130 has been engaged, the suture catch mechanism 106 and engaged suture portion 130 are then retracted through the tissue of the first leaflet 132A into the distal assembly 102, as shown in FIG. 21. The device 100 can be advanced slightly so that the suture clasp arm 104 can be moved to the retracted position without pinching the first leaflet 132A. The first suturing device 100 can then be withdrawn from the valve.

Figure 22:
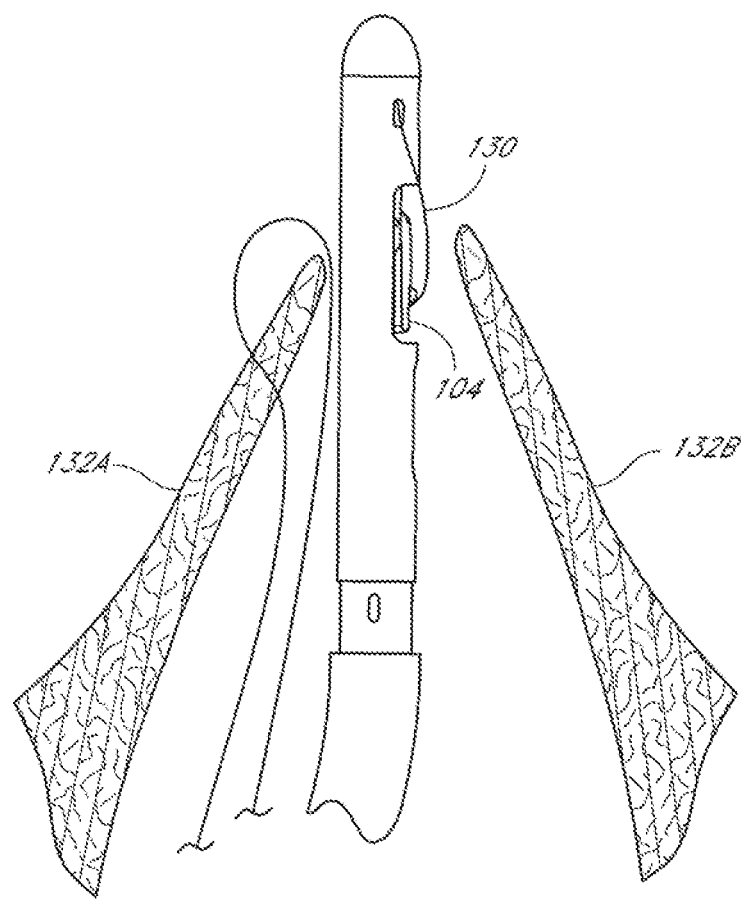
FIG. 22 is a schematic representation as in FIG. 21 showing a second suturing device positioned in the passage through the valve.
Figure 23:
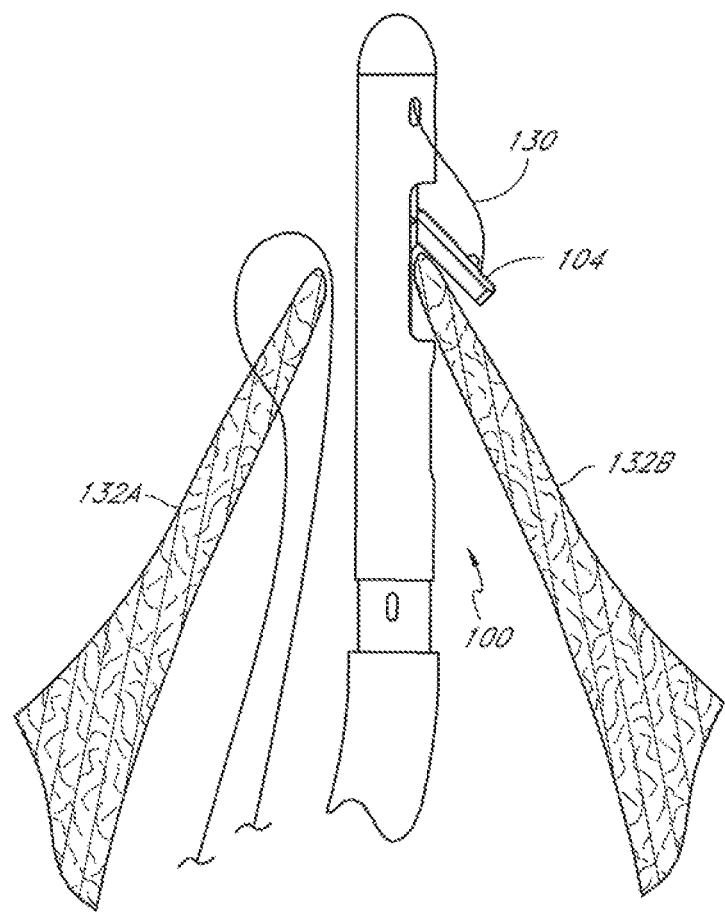
FIG. 23 is a schematic representation as in FIG. 22 with the suture clasp arm positioned around a second leaflet of the valve.

A second suturing device 100 can then be advanced into the heart and positioned between the leaflets 132A, 132B of the valve, as shown in FIG. 22. The suture clasp arm 104 can then be extended and the device 100 can be advanced such that the suture clasp arm 104 extends around the tip of the second leaflet 132B, as shown in FIG. 23.

Figure 24:
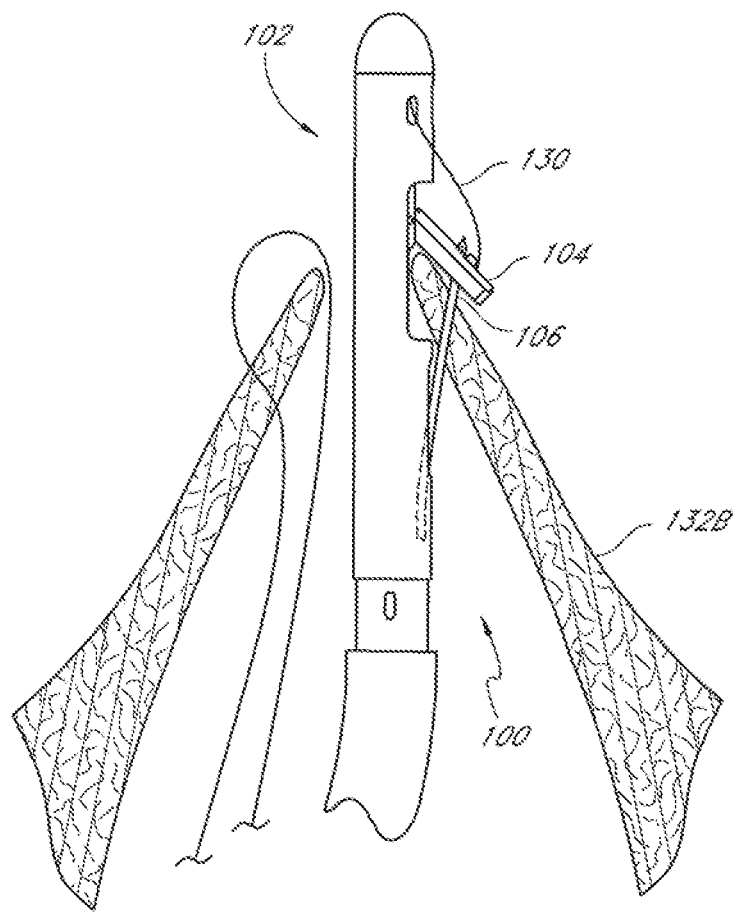
FIG. 24 is a schematic representation as in FIG. 23 showing a suture catch mechanism engaging the suture clasp arm.

Once the suture clasp arm 104 has been properly positioned around the second leaflet 132B, the suture catch mechanism 106 can be advanced from the distal assembly 102 to penetrate the second leaflet 132B and engage the suture portion 130 held by the suture clasp arm 104, as illustrated in FIG. 24. As noted above with respect to the first leaflet 132A, in some embodiments, the suture clasp arm 104 can be moved to the retracted position to securely hold a portion of the second leaflet 132B between the arm 104 and the distal assembly 102 before the suture catch mechanism 106 is advanced through the second leaflet 132B to engage the suture portion 130.

Figure 25:
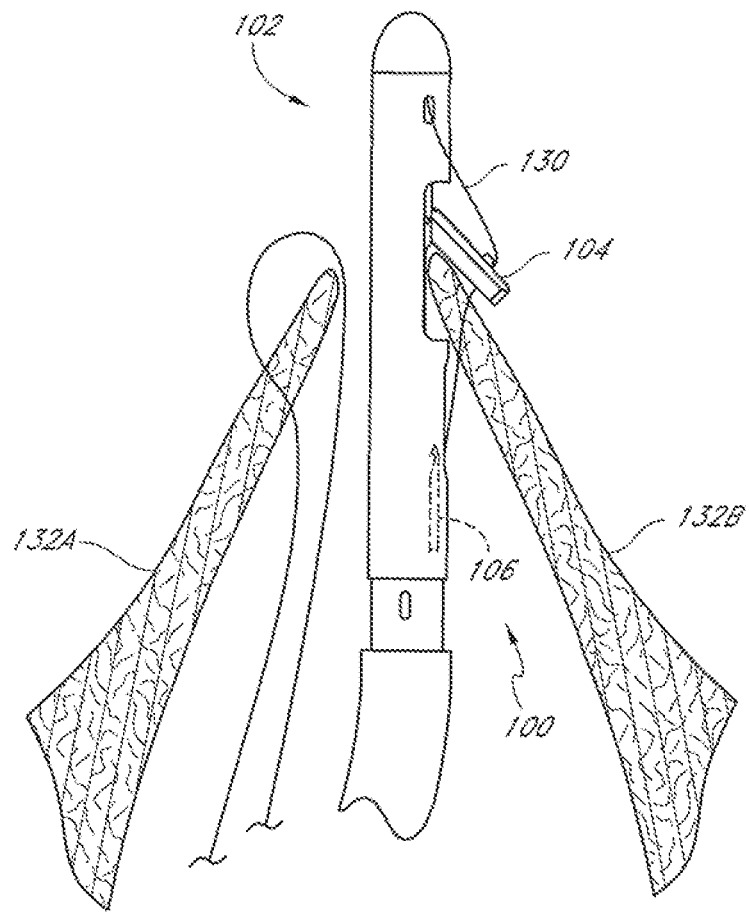
FIG. 25 is a schematic representation as in FIG. 24 showing the suture catch mechanism and a suture portion retracted through the second leaflet.

After the suture portion 130 has been engaged, the suture catch mechanism 106 and engaged suture portion 130 are then retracted through the tissue of the second leaflet 132B into the distal assembly 102, as illustrated in FIG. 25. The suture clasp arm 104 can then be closed after slightly advancing the device 100 to avoid pinching the second leaflet 132B as the arm 104 is closed. Once the suture clasp arm 104 is closed, the suturing device 100 can be withdrawn from the patient's heart.

Figure 26:
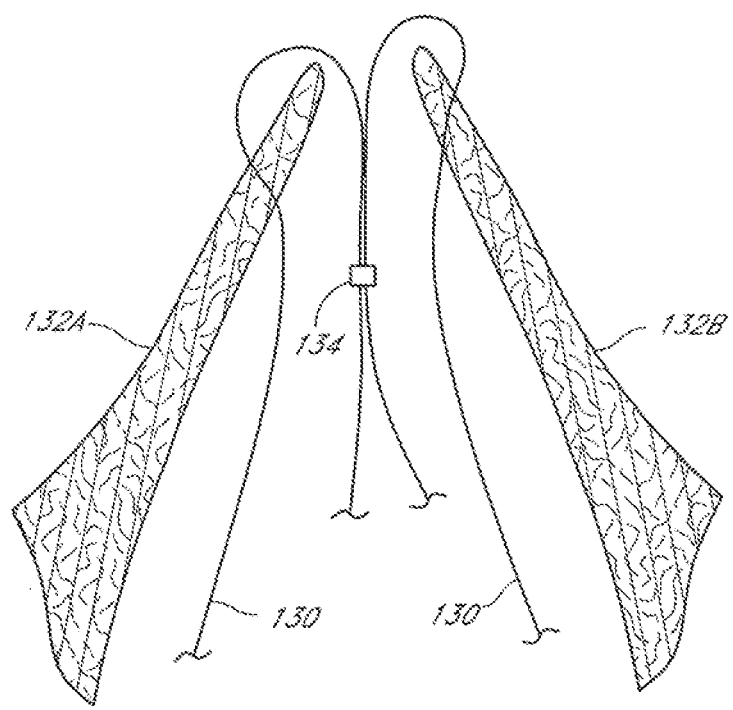
FIG. 26 is a schematic representation as in FIG. 25 showing the suture portions extending through the first leaflet and the second leaflet and being joined by a first knot.

As shown in FIG. 26, after the suturing device 100 has been withdrawn, the suture portions 130 will extend proximally from the leaflets 132A, 132B. The suture portions 130 can then be secured together, as illustrated in FIG. 26, by tying a knot 134 according to any known method or by applying a knot 134. The suture portions 130 can be secured together exterior to the body or within the body. Any excess portion of sutures 130 can be trimmed. The suture portions 130 can and can then be pulled to draw the first leaflet 132A and the second leaflet 132B towards one another. A second knot can then be tied or applied to the sutures 130 to limit movement of the leaflets 132A, 132B relative to one another, as described above. In some embodiments, the sutures 130 can hold a portion of the leaflets 132A, 132B in contact with one another. In other embodiments, the sutures 130 merely hold the leaflets 132A, 132B in closer proximity to one another than they had previously been.

When a device 100 having plural arms 104 and plural suture catch mechanisms 106 is used, the device 100 can be configured to place a single suture 130 through both the first leaflet 132A and the second leaflet 132B. The single suture 130 can be placed through the first and second leaflets 132 either simultaneously or sequentially. In some embodiments, the suture portions 130 can be pulled to draw the first leaflet 132A and the second leaflet 132B towards one another without applying a knot to the suture 130 beforehand. Accordingly, a single knot 134 can be applied to the suture 130 to hold the leaflets 132A, 132B in proximity to one another.

Figure 27:
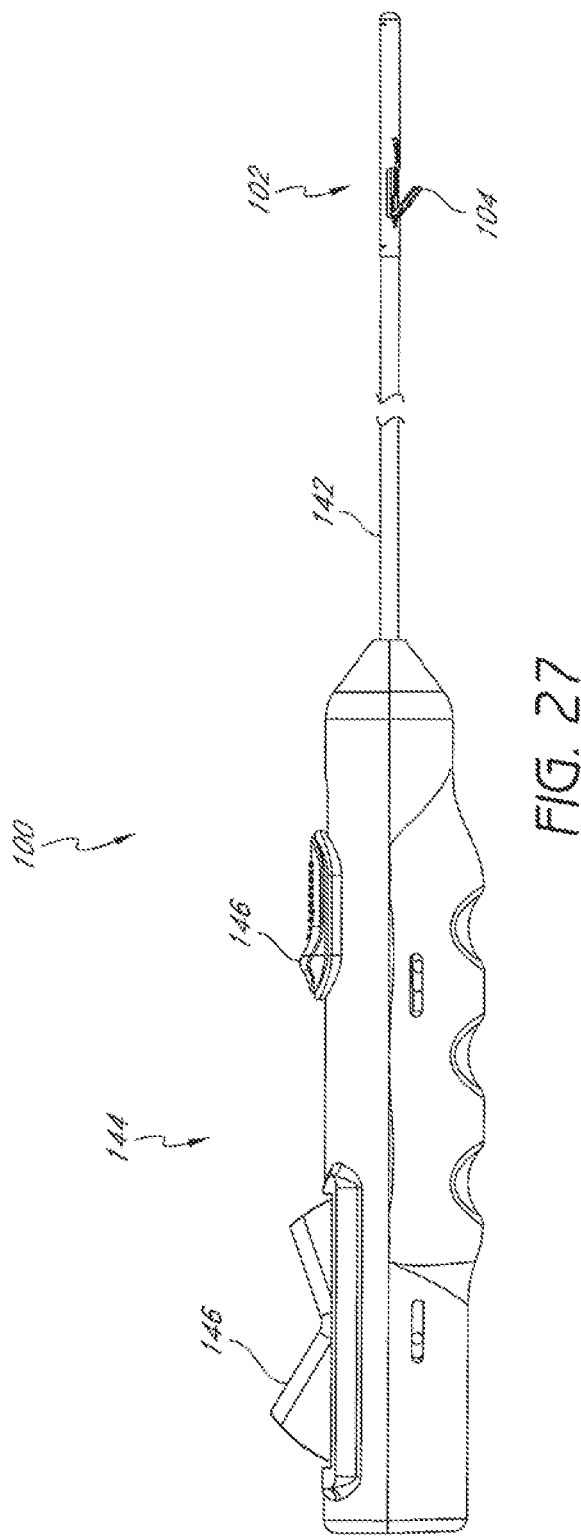
FIG. 27 is a plan view of an embodiment of a suturing device with a suture clasp arm in an extended position.
Figure 28:
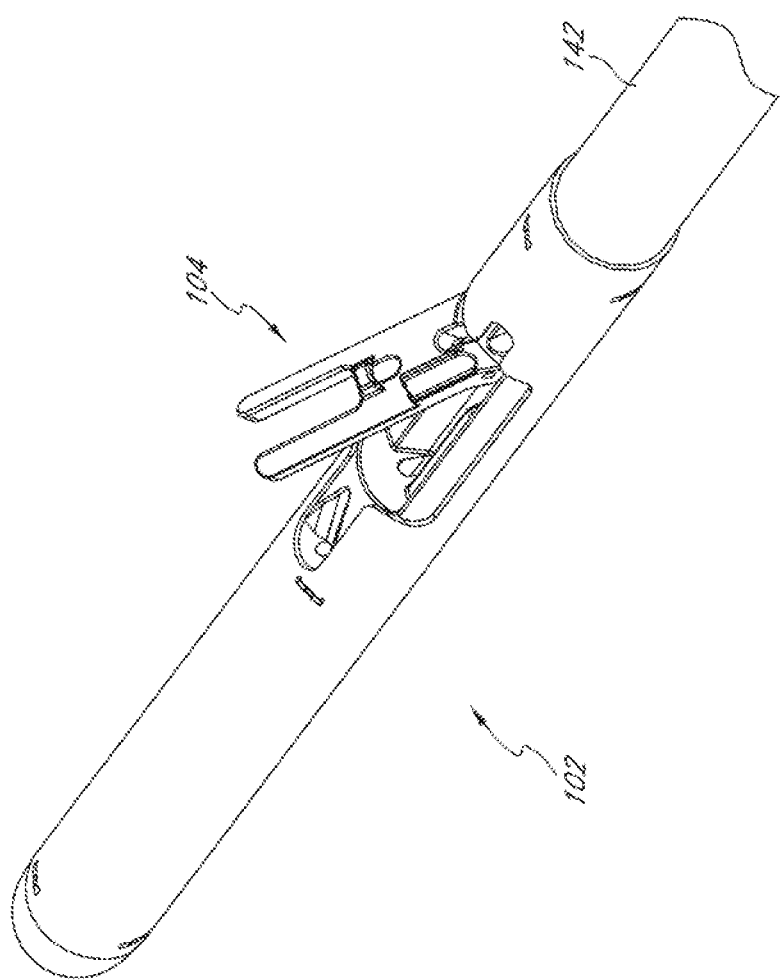
FIG. 28 is an enlarged perspective view of the distal end of the suturing device of FIG. 27 with the suture clasp arm in an extended position.

FIGS. 27 and 28 illustrate an embodiment of a suturing device 100 that can be used to suture an anatomical valve, such as a heart valve. The suture device 100 illustrated in FIGS. 27 and 28 is similar is some respects to the suturing devices 100 illustrated and described above. For example, the suturing device 100 of FIGS. 27 and 28, like the suturing device 100 of FIGS. 16 and 17, can comprise a distal assembly 102, a single suture clasp arm 104, and a single suture catch mechanism 106.

As illustrated in FIGS. 27 and 28, the suturing device 100 can comprise an elongate member 142 to facilitate manipulation of the suture clasp arm 104 and the suture catch mechanism 106 from a remote location. For example, the elongate member can comprise one or more lumens to accommodate a length of suture, or one or more actuator rods for manipulating the suture clasp arm 104 and the suture catch mechanism 106, or both. The suturing device 100 can comprise a handle with one or more actuators and/or pulls 146 for moving the suture clasp arm 104 and the suture catch mechanism 106. Further details regarding handles and associated components, including actuator rods, are provided in U.S. Patent Application Publication No. 2008/0269786, published on Oct. 30, 2008, the entirety of which is hereby incorporated by reference herein and forms a part of this specification.

In some embodiments, the suture clasp arm 104 can pivot about an axis located at a proximal end of the suture clasp arm 104 when the suture clasp arm 104 is in a retracted position, as illustrated in FIGS. 16 and 17.

A method of suturing anatomical valves is illustrated in FIGS. 29-37. Although the illustrated method involves two devices 100, each having a single suture clasp arm 104 and a single suture catch mechanism 106, the illustrated method can also be practiced using a device 100 having more than one arm 104 and more than one suture catch mechanism 106, as discussed above, for example.

Figure 29:
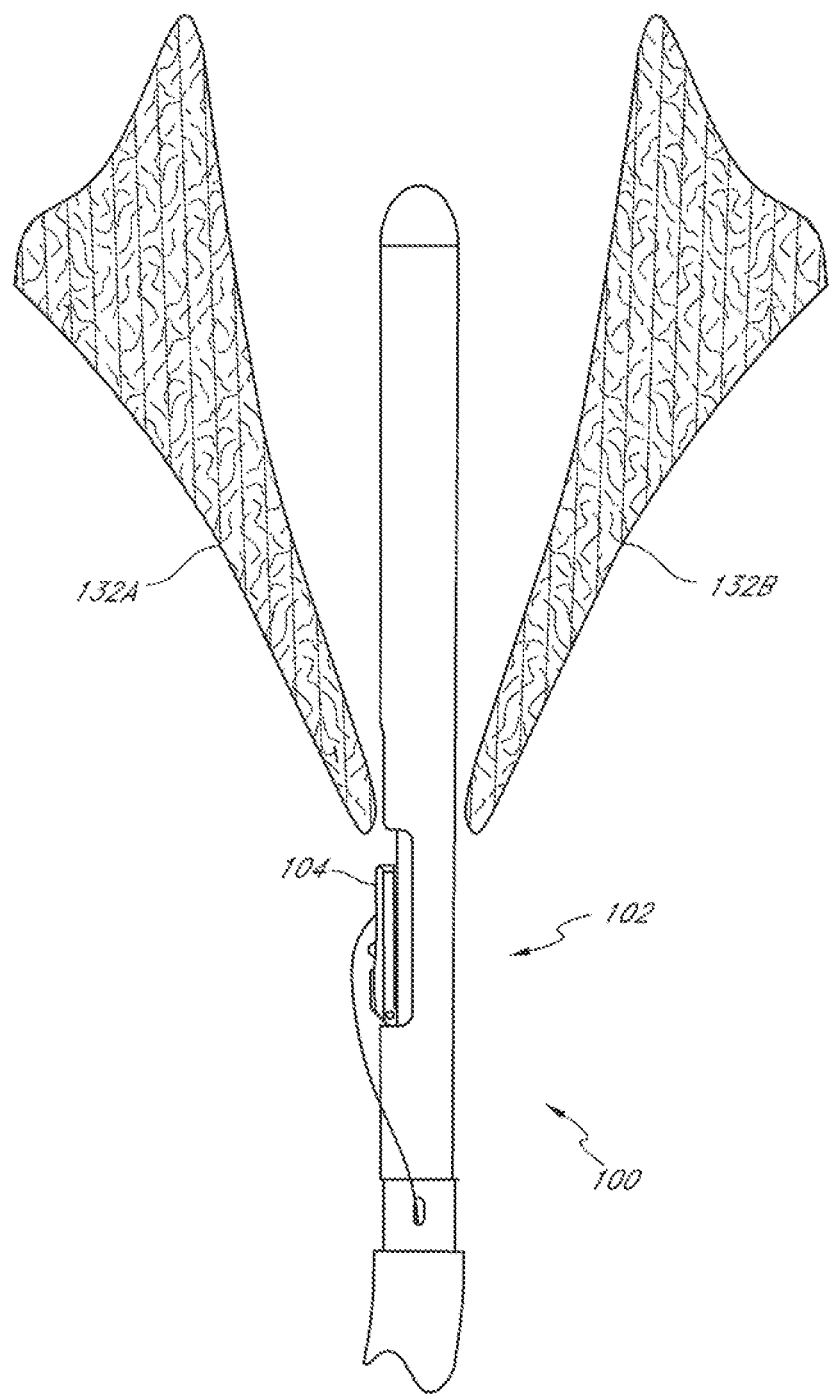
FIG. 29 is a schematic representation of an embodiment of a first suturing device positioned in a passage through a valve.

The distal end of a first suturing device 100 can be positioned between leaflets 132 of a valve, as shown in FIG. 29. The device 100 can be advanced through the vasculature to the desired position. For example, the device 100 can be advanced through a subclavian artery into the aorta to position the device 100 in the passage through the aortic valve 4 (FIG. 1). Alternatively, the device 100 can be inserted through a puncture or small incision 9 in the heart to position the device 100 in the passage through the mitral valve 8, as shown in FIG. 2. Such a puncture can be located at or near the apex of the heart 7.

Figure 30:
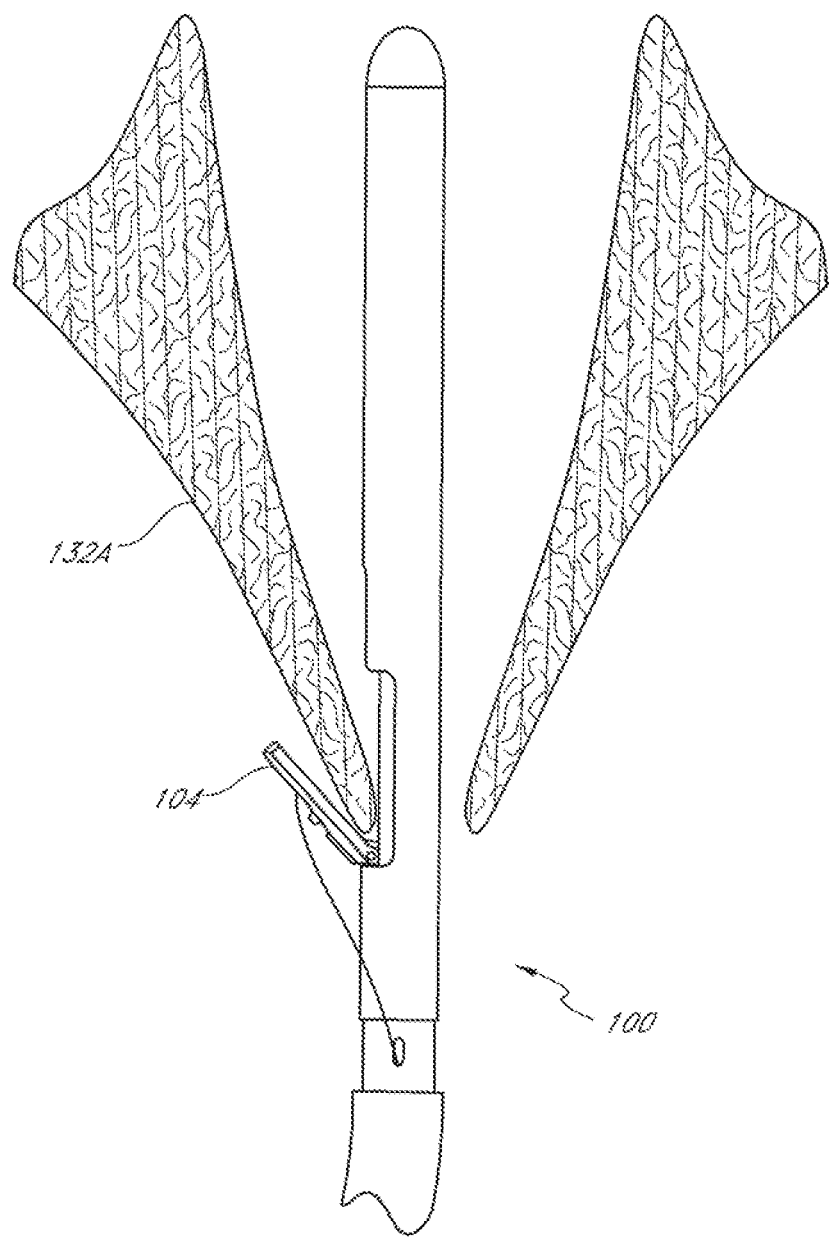
FIG. 30 is a schematic representation as in FIG. 29 with a suture clasp arm positioned around a first leaflet of the valve.

As illustrated in FIG. 29, the suturing device 100 can be positioned to allow a suture clasp arm 104 to extend from the distal assembly 102. The suture clasp arm 104 can then be extended and the device 100 can be advanced until the suture clasp arm 104 extends around a first leaflet 132A of the valve, as shown in FIG. 30.

Figure 31:
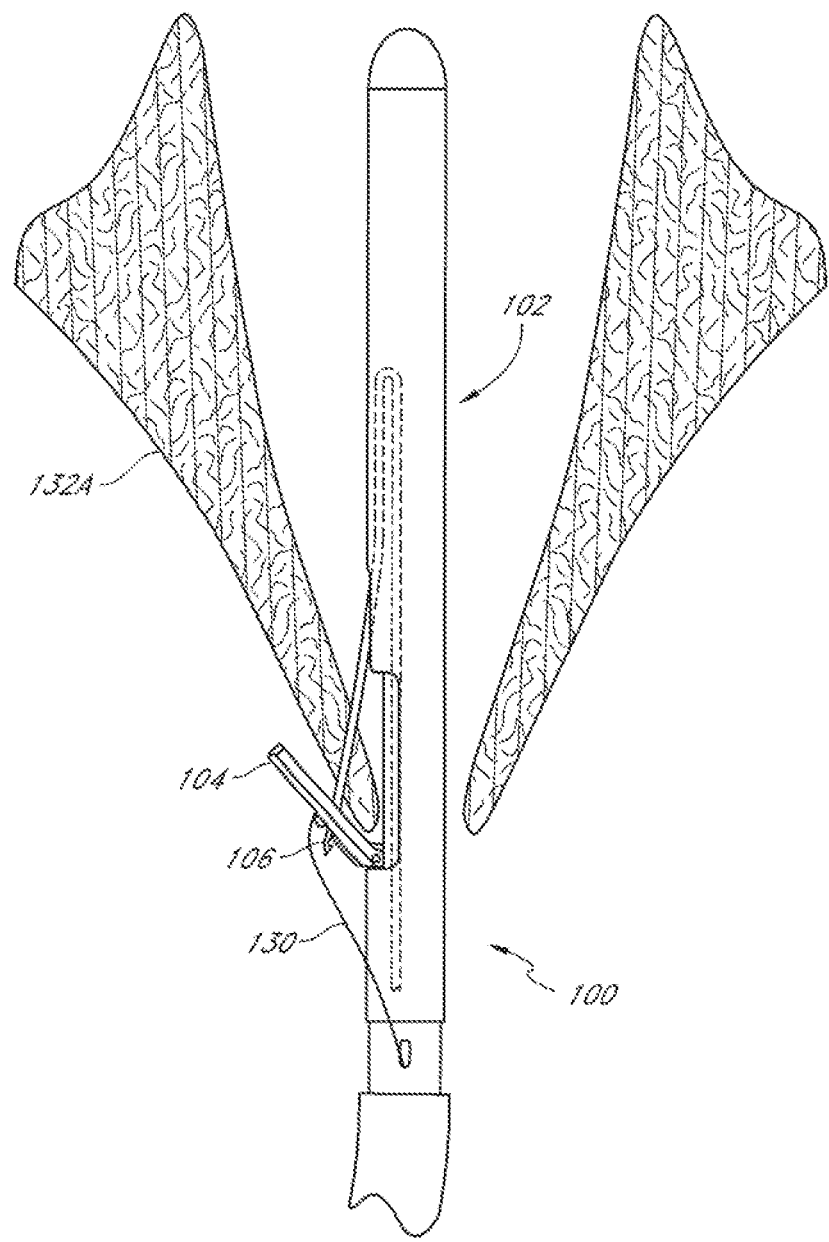
FIG. 31 is a schematic representation as in FIG. 30 showing a suture catch mechanism engaging the suture clasp arm.

Once the suture clasp arm 104 has been properly positioned around the first leaflet 132A, the suture catch mechanism 106 can be advanced from the distal assembly 102 to penetrate the first leaflet 132A and engage the suture portion 130 held by the suture clasp arm 104, as illustrated in FIG. 31. In some embodiments, the suture clasp arm 104 can be moved to the retracted position to securely hold a portion of the first leaflet 132A between the arm 104 and the distal assembly 102 before the suture catch mechanism 106 is advanced through the first leaflet 132A to engage the suture end, as described above, for example.

Figure 32:
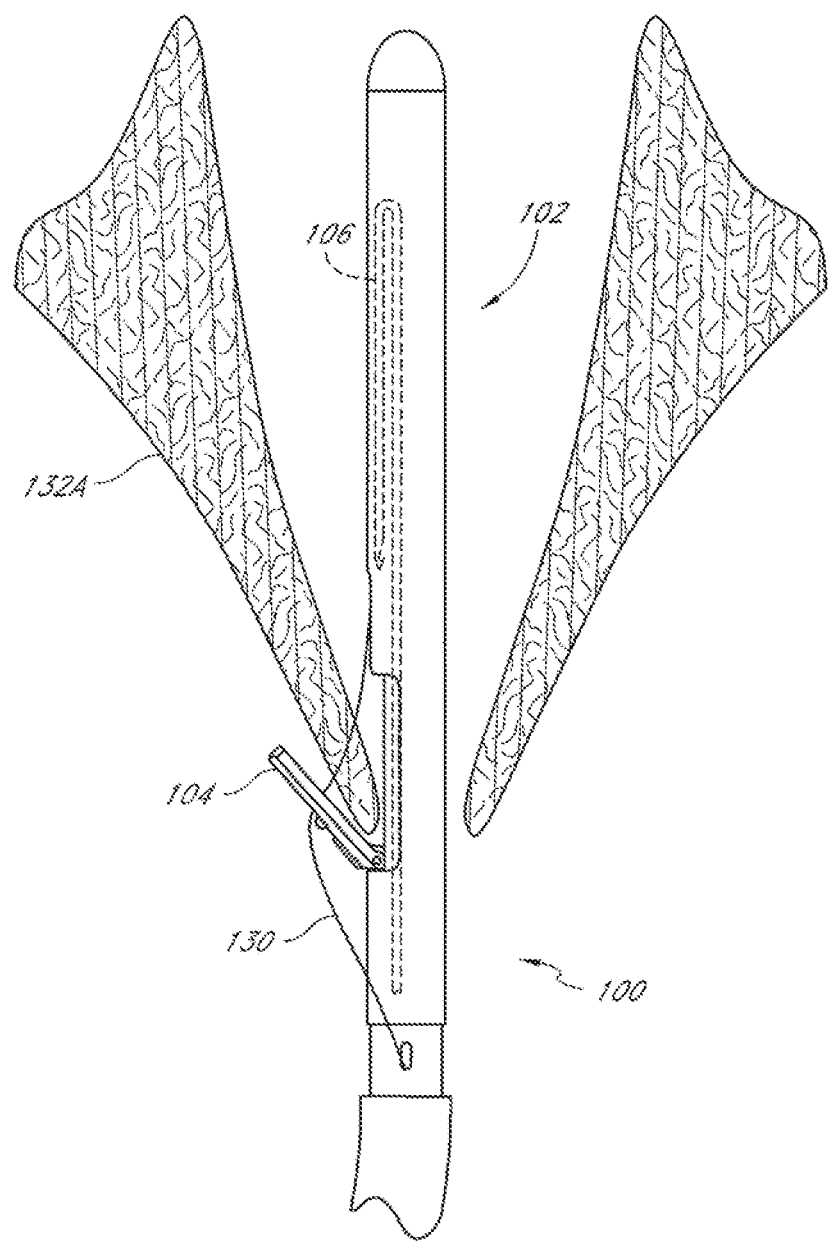
FIG. 32 is a schematic representation as in FIG. 31 showing the suture catch mechanism and a suture portion retracted through the first leaflet.

As shown in FIG. 32, once the suture portion 130 has been engaged, the suture catch mechanism 106 and engaged suture portion 130 are then retracted through the tissue of the first leaflet 132A into the distal assembly 102. The device 100 can be retracted slightly so that the suture clasp arm 104 can be moved to the retracted position without pinching the first leaflet 132A. The first suturing device 100 can then be withdrawn from the valve.

Figure 33:
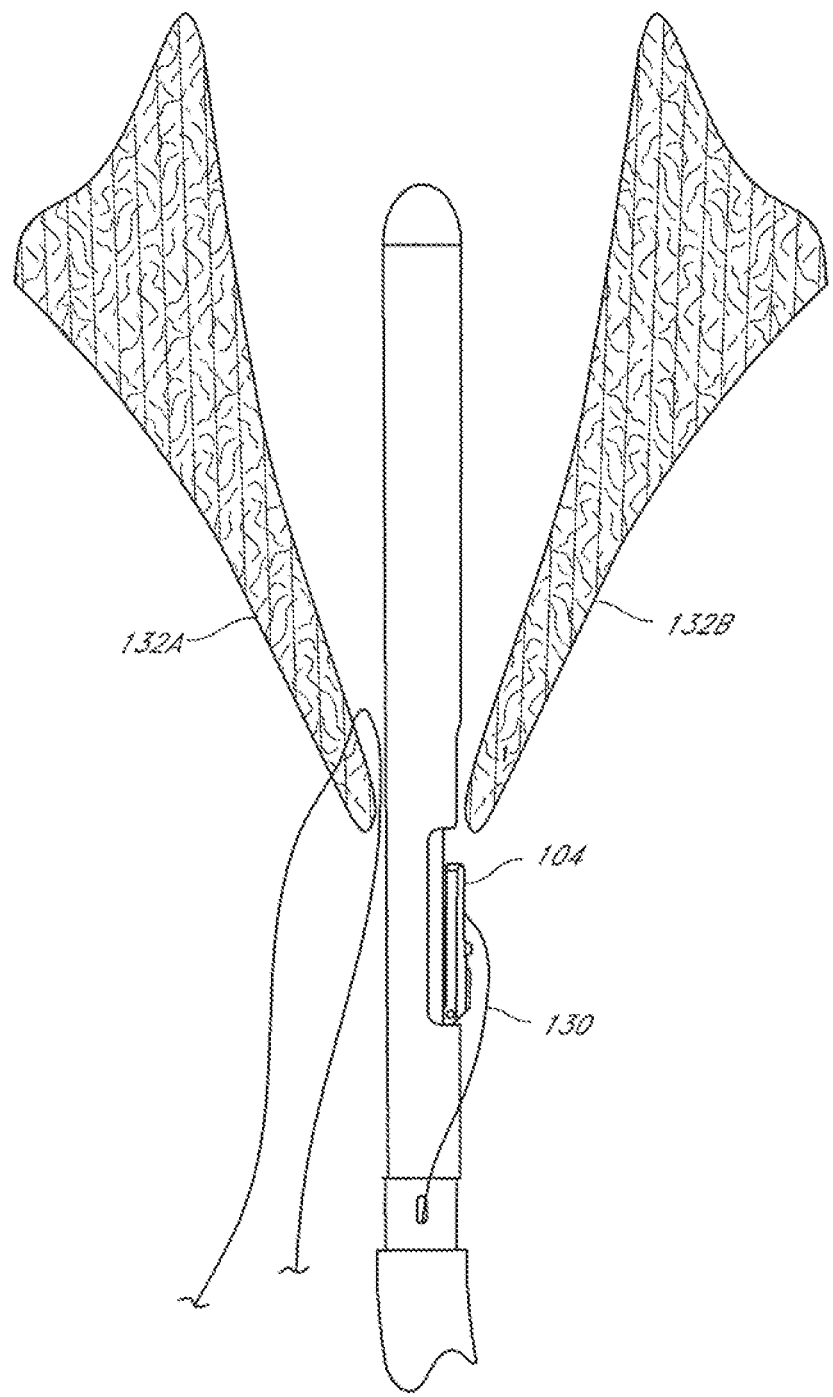
FIG. 33 is a schematic representation as in FIG. 32 showing a second suturing device positioned in the passage through the valve so as to permit a suture clasp arm to extend from the second suturing device.
Figure 34:
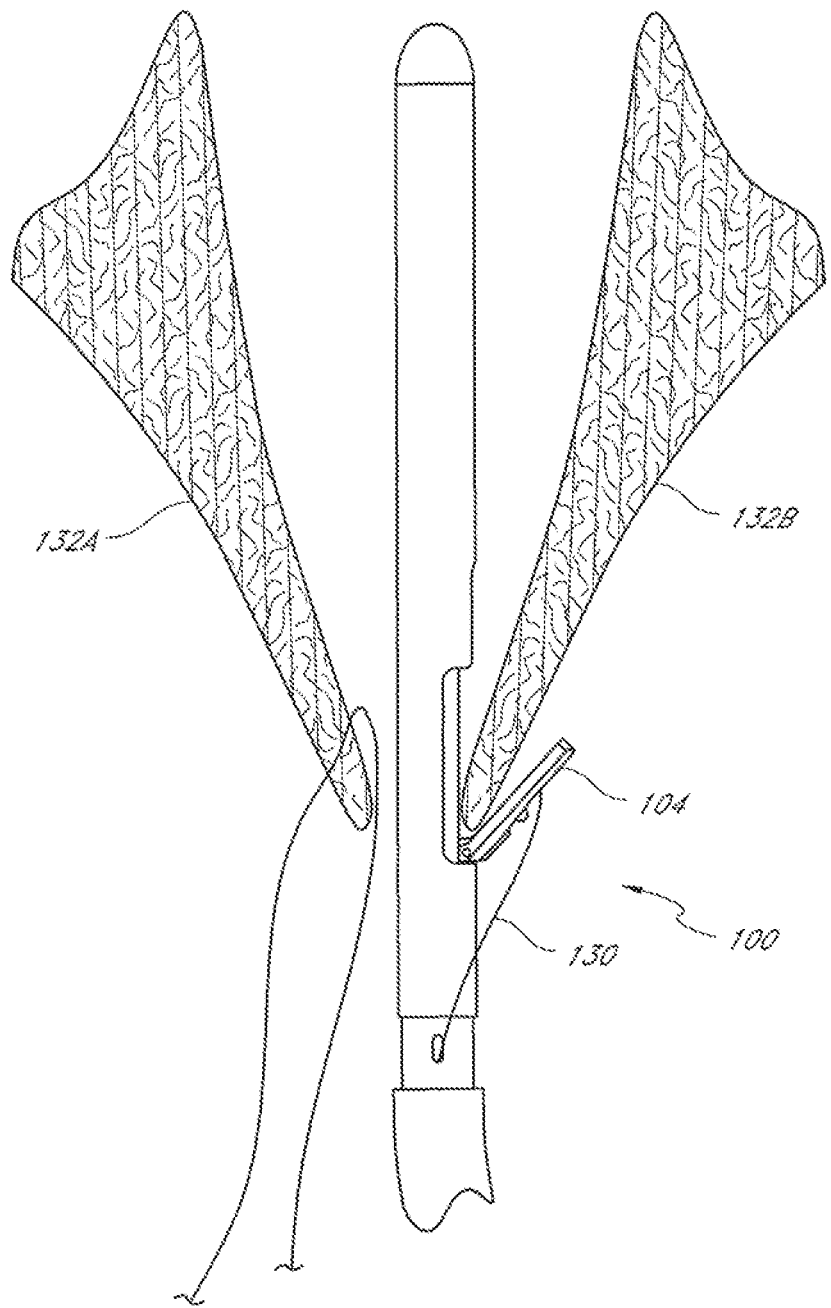
FIG. 34 is a schematic representation as in FIG. 33 with the suture clasp arm positioned around a second leaflet of the valve.

A second suturing device 100 can then be advanced into the heart and positioned between the leaflets 132A, 132B of the valve, as shown in FIG. 33. The suture clasp arm 104 can then be extended and the device 100 can be advanced such that the suture clasp arm 104 extends around the tip of the second leaflet 132B, as shown in FIG. 34.

Figure 35:
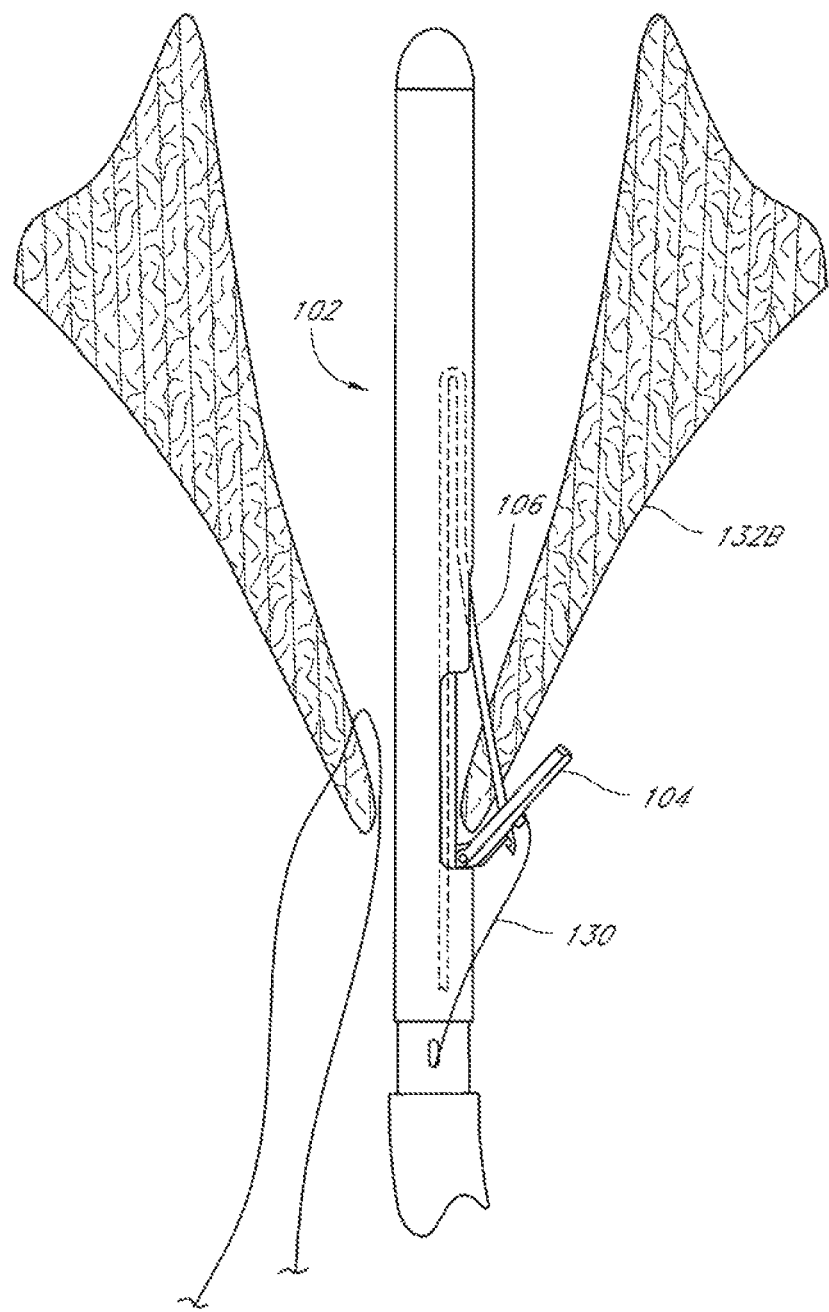
FIG. 35 is a schematic representation as in FIG. 34 showing a suture catch mechanism engaging the suture clasp arm.

In the illustrated embodiment, once the suture clasp arm 104 has been properly positioned around the second leaflet 132B, the suture catch mechanism 106 can be advanced from the distal assembly 102 to penetrate the second leaflet 132B and engage the suture portion 130 held by the suture clasp arm 104, as illustrated in FIG. 35. As noted above with respect to the first leaflet 132A, in some embodiments, the suture clasp arm 104 can be moved to the retracted position to securely hold a portion of the second leaflet 132B between the arm 104 and the distal assembly 102 before the suture catch mechanism 106 is advanced through the second leaflet 132B to engage the suture portion 130.

Figure 36:
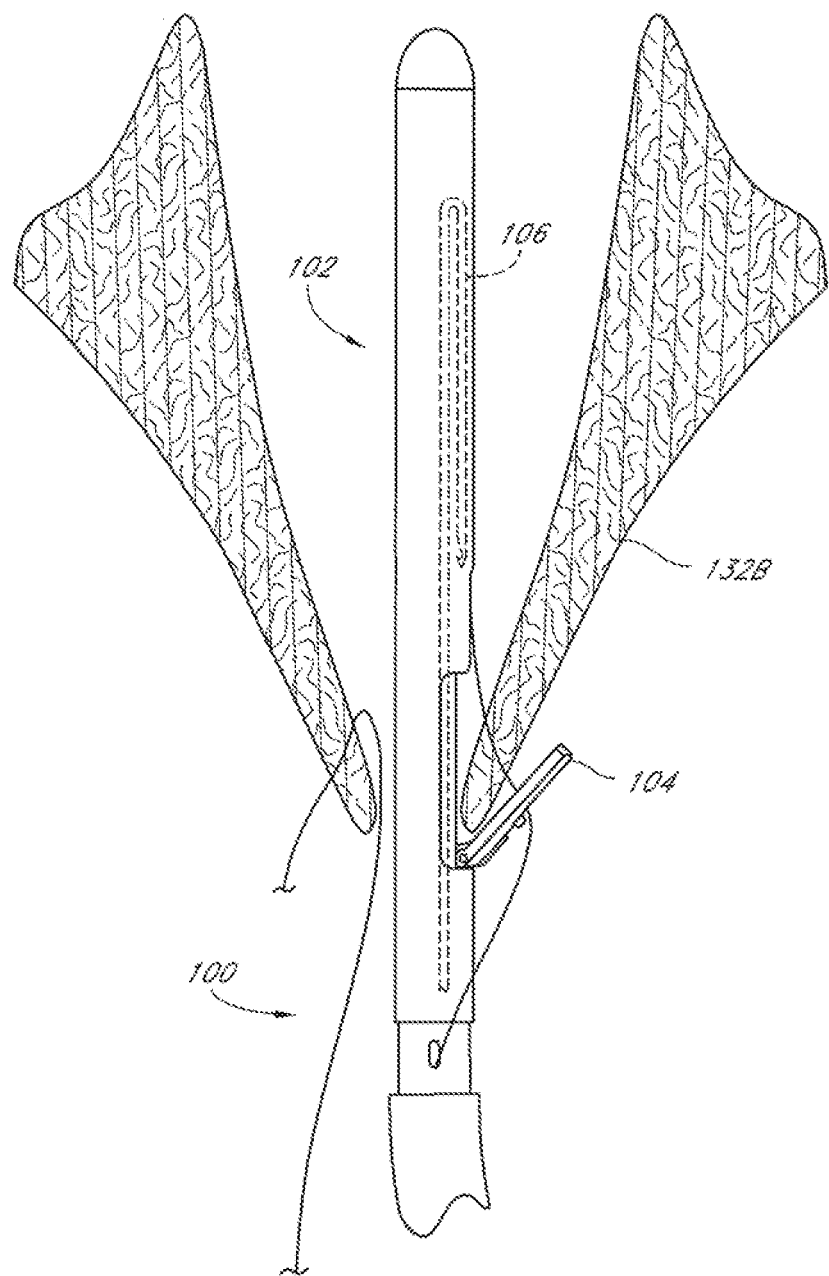
FIG. 36 is a schematic representation as in FIG. 35 showing the suture catch mechanism and a suture portion retracted through the second leaflet.

After the suture portion 130 has been engaged, the suture catch mechanism 106 and engaged suture portion 130 are then retracted distally through the tissue of the second leaflet 132B into the distal assembly 102, as illustrated in FIG. 36. The suture clasp arm 104 can then be closed after slightly retracting the device 100 to avoid pinching the second leaflet 132B. Once the suture clasp arm 104 is closed, the suturing device 100 can be withdrawn from the patient's heart.

Figure 37:
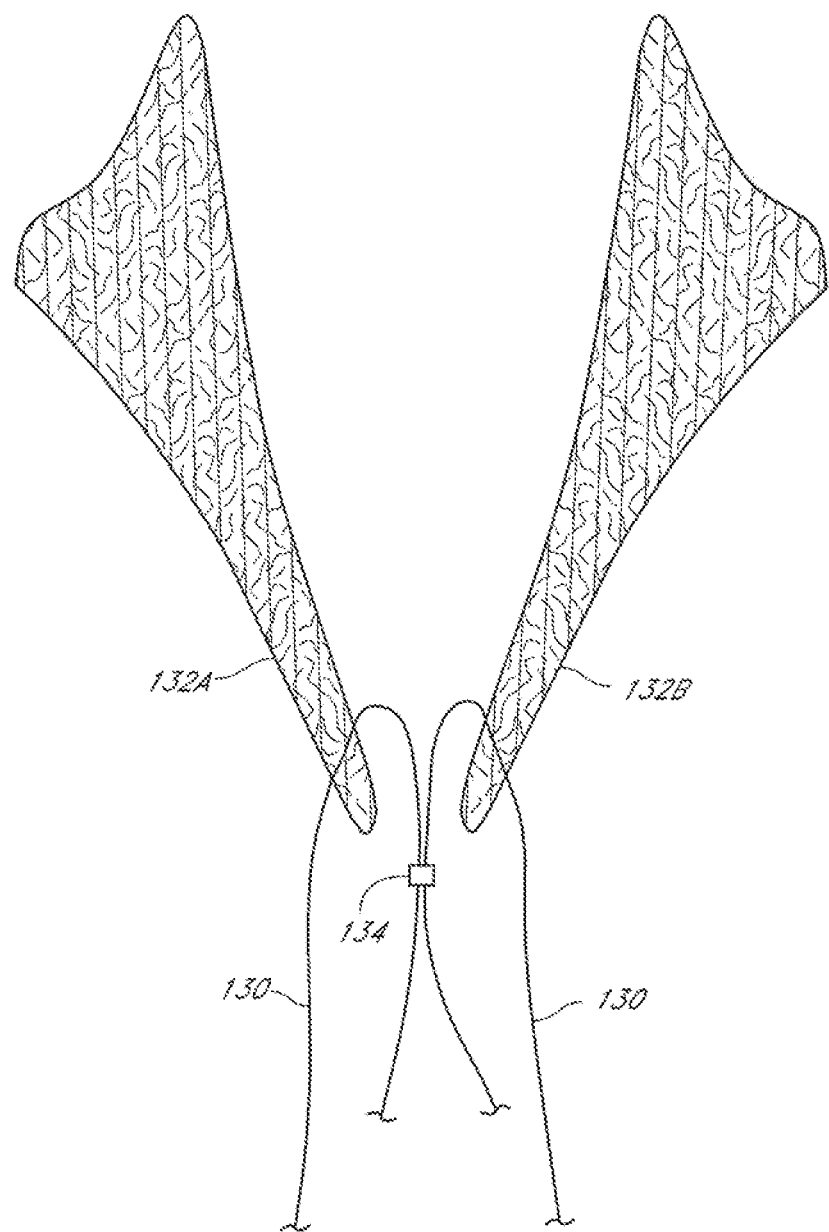
FIG. 37 is a schematic representation as in FIG. 36 showing the suture portions extending through the first leaflet and the second leaflet and being joined by a first knot.

As shown in FIG. 37, after the suturing device 100 has been withdrawn, the suture portions 130 will extend proximally from the leaflets 132A, 132B. The suture portions 130 can then be secured together, as illustrated in FIG. 37, by tying a knot 134 according to any known method or by applying a knot 134. The suture portions 130 can be secured together exterior to the body or within the body. Any excess portion of sutures 130 can be trimmed. The suture portions 130 can and can then be pulled to draw the first leaflet 132A and the second leaflet 132B towards one another. A second knot can then be tied or applied to the sutures 130 to limit movement of the leaflets 132A, 132B relative to one another. In some embodiments, the sutures 130 can hold a portion of the leaflets 132A, 132B in contact with one another. In other embodiments, the sutures 130 merely hold the leaflets 132A, 132B in closer proximity to one another than they had previously been.

When a device 100 having plural arms 104 and plural suture catch mechanisms 106 is used, the device 100 can be configured to place a single suture 130 through both the first leaflet 132A and the second leaflet 132B, either simultaneously or sequentially. In some such embodiments, the suture portions 130 can be pulled to draw the first leaflet 132A and the second leaflet 132B towards one another without applying a knot to the suture 130 beforehand. Accordingly, a single knot 134 can be applied to the suture 130 to hold the leaflets 132A, 132B in proximity to one another.

Figure 38:
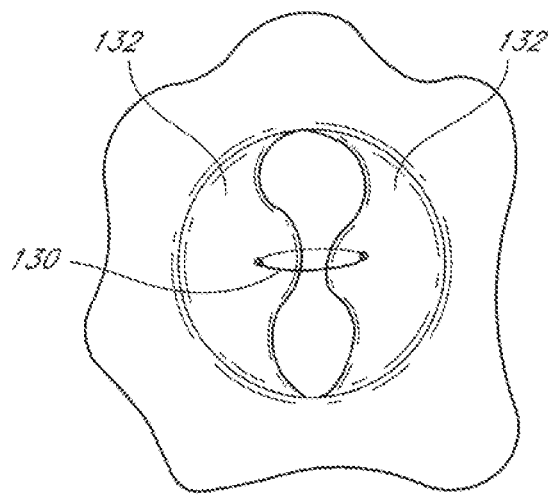
FIG. 38 illustrates placement of suture through a bicuspid valve near a central portion of each leaflet.
Figure 39:
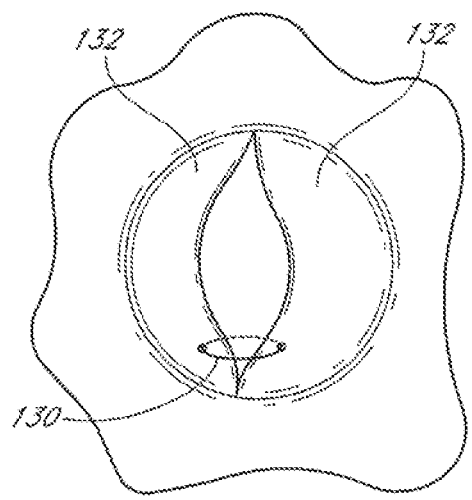
FIG. 39 illustrates placement of suture through a bicuspid valve at locations spaced from the center of each leaflet.
Figure 40:
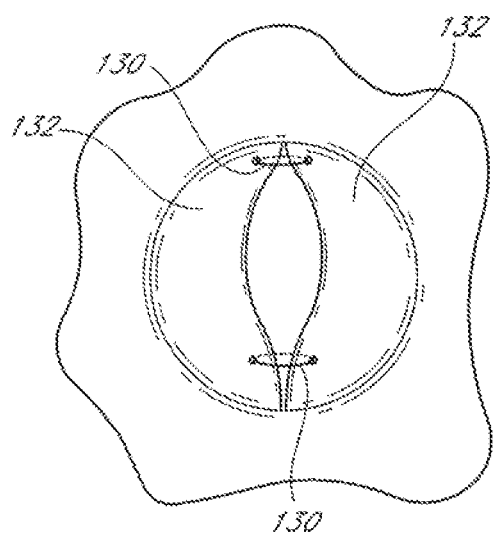
FIG. 40 illustrates placement of suture through a bicuspid valve at multiple locations spaced from the center of each leaflet.
Figure 41:
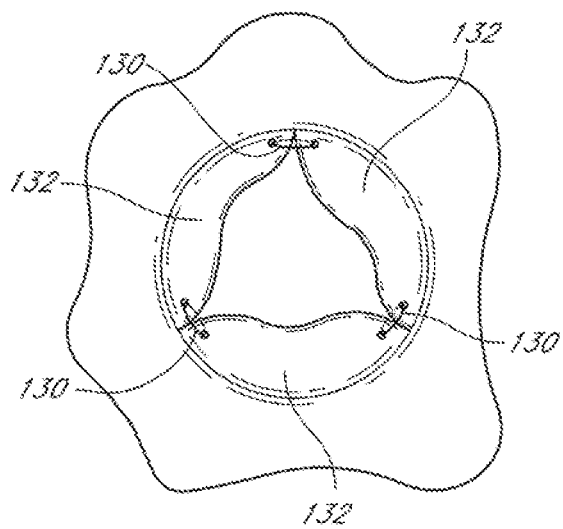
FIG. 41 illustrates placement of suture through a tricuspid valve.

The suture or sutures 130 can be placed through the leaflets 132 at locations selected by the physician to treat a problem of a particular valve. For example, in some embodiments, a suture or sutures 130 can be passed through the leaflets 132 at locations in or near a central region of the leaflets 132, as illustrated in FIG. 38. In some embodiments, a suture or sutures 130 can be passed through a portion of the leaflets 132 that is in proximity to a periphery of the valve, as illustrated in FIG. 39. In some embodiments, sutures 130 can be applied to multiple locations between two leaflets 132, as illustrated in FIG. 40. In some embodiments, sutures 130 can be applied to multiple locations between more than two leaflets 132, as illustrated in FIG. 41 with respect to a tricuspid valve.

Figure 42:
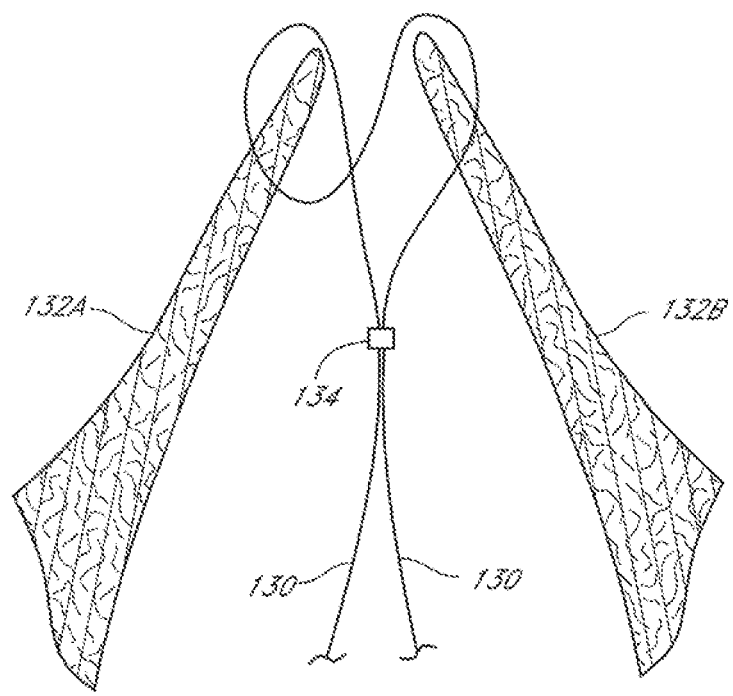
FIG. 42 illustrates placement of suture through a valve.
Figure 43:
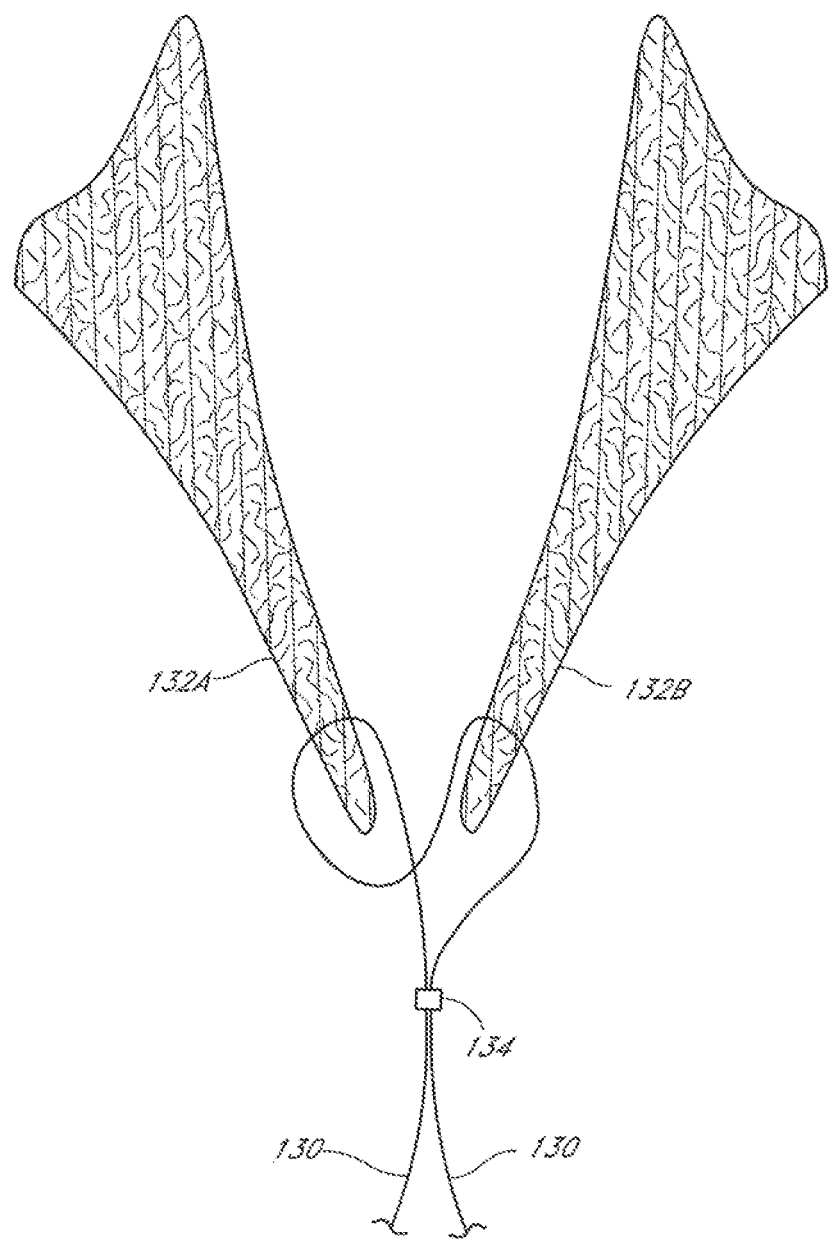
FIG. 43 illustrates placement of suture through a valve.

FIGS. 42 and 43 illustrate other manners of placing suture through leaflets of a valve. In some embodiments, suture can be placed as shown in FIG. 42 or 43 using the devices 100 illustrated in FIGS. 16-17 and 27-28. The devices 100 can be introduced through the same or different access routes. For example, one device can be introduced to the heart through the vasculature while another device is introduced transapically. In some embodiments, a first suture can be placed through a first leaflet by a first device 100 as illustrated in FIGS. 18-21 and a second suture can be placed through a second leaflet by a second device 100 as illustrated in FIGS. 29-32. The second suture can be placed before the first suture in some embodiments. In embodiments involving the placement of multiple sutures, the multiple sutures can be joined with a single knot or with multiple knots. Further information regarding devices and methods for placing suture as shown in FIGS. 42 and 43 is provided in the incorporated by reference U.S. Patent Application Publication No. 2008/0269786, published on Oct. 30, 2008, and, in particular, the embodiments described in association with FIGS. 10I-L, 27-28B, 36-39A-K.

Figure 44:
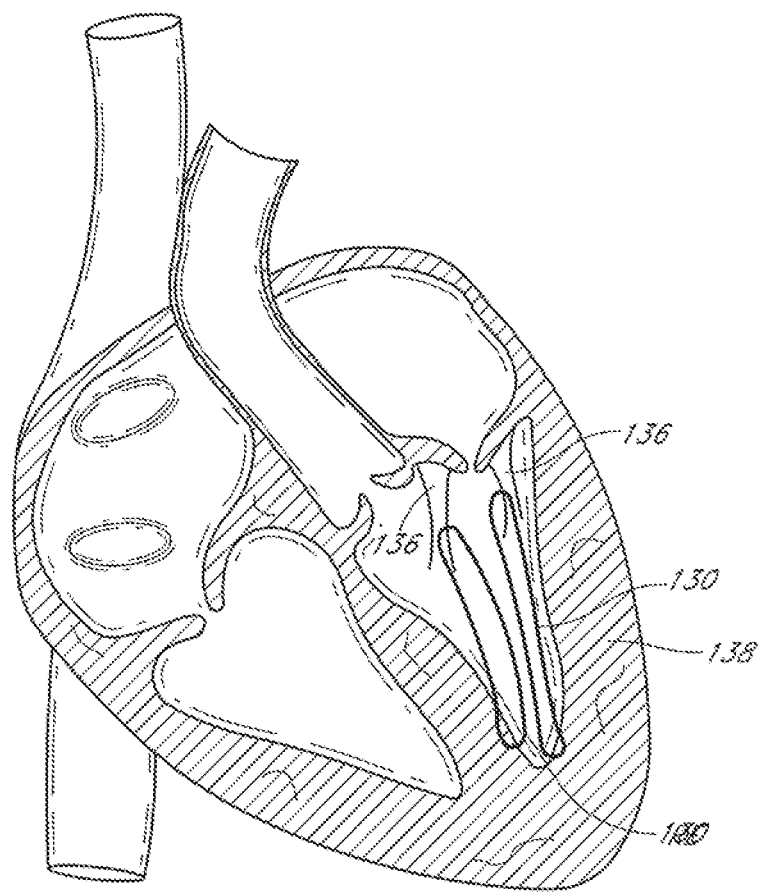
FIG. 44 illustrates placement of suture through chordae tendineae and myocardium.

The devices and methods described and referenced herein can be used to perform other techniques for valve repair. For example, the devices and methods described above can be used to apply a suture to one or more of the chordae tendineae 136 and myocardium 138, as illustrated in FIG. 44, to restore tension to chordae tendineae that have been come elongated. The devices and methods described above can be used to suture a patch to natural or surgically-created openings in leaflets. The devices and methods described above can be used to attach a ring around the outside of the malfunctioning valve. The devices and methods described above can be used to suture prosthetics to the heart.

Although the foregoing description of the preferred embodiments has shown, described and pointed out the fundamental novel features of the invention, it will be understood that various omissions, substitutions, and changes in the form of the detail of the apparatus as illustrated as well as the uses thereof, may be made by those skilled in the art, without departing from the spirit of the invention. For example, while the suturing device is described with respect to suturing a valve of a patient's heart, it is further envisioned that the suturing device could used to close or reduce a variety of other tissue openings, lumens, hollow organs or natural or surgically created passageways in the body. The suturing device can have any suitable number of arms, such as two or four or more, and any given arm can have one or more suture clasps or openings.

What is claimed is:

1. A device for suturing an anatomic valve, the device comprising:
    an elongate body having a proximal end and a distal end;
    a first needle operatively coupled to the elongate body near the distal end of the elongate body for movement between a withdrawn position and an advanced position;
    a first arm attached to the elongate body near the distal end of the elongate body for movement between a retracted position and an extended position, the first arm being at a greater angle with the elongate body in the extended position than in the retracted position, the first arm comprising a suture mount for releasably retaining a suture portion, the suture mount being positioned on the first arm such that the first needle retrieves the suture portion retained in the suture mount when the first needle is moved from the withdrawn position to the advanced position and returned to the withdrawn position, a tissue-piercing structure of the first needle being received within the first arm when the first arm is at least partially retracted from the extended position and the first needle is in the advanced position; and
    at least a second arm and at least a second needle,
    wherein a recess is defined between the elongate body and the first arm, the recess being sized and shaped to receive a leaflet of a valve between the distal end of the elongate body and the first arm without damaging the leaflet;
    wherein the first needle is configured to penetrate the leaflet of the valve as the first needle moves to the advanced position when the leaflet is between the distal end of the elongate body and the first arm.

2. The device of claim 1, wherein the recess is sized and shaped to retain the leaflet between the elongate body and the first arm when the first arm is at least partially retracted from the extended position without damaging the leaflet.

3. The device of claim 1, wherein the suture mount is positioned on the first arm such that the first needle retrieves the suture portion retained in the suture mount when the first needle is moved from the withdrawn position to the advanced position and returned to the withdrawn position while the first arm is at least partially retracted from the extended position.

4. The device of claim 1, wherein the second needle is operatively coupled to the elongate body near the distal end of the elongate body for movement between a withdrawn position and an advanced position.

5. The device of claim 4, wherein the second arm is attached to the elongate body near the distal end of the elongate body for movement between a retracted position and an extended position, the second arm being at a greater angle with the elongate body in the extended position than in the retracted position, the second arm comprising a second suture mount for releasably retaining a second suture portion, the second suture mount being positioned on the second arm such that the second needle retrieves the second suture portion retained in the second suture mount when the second needle is moved from the withdrawn position to the advanced position and returned to the withdrawn position.

6. The device of claim 5, wherein a tissue-piercing structure of the second needle is received within the second arm when the second arm is at least partially retracted from the extended position and the second needle is in the advanced position.

7. The device of claim 5, wherein a second recess is defined between the elongate body and the second arm, the second recess being sized and shaped to retain a second leaflet between the elongate body and the second arm when the second arm is at least partially retracted from the extended position without damaging the second leaflet.

8. The device of claim 5, wherein the second suture mount is positioned on the second arm such that the second needle retrieves the suture portion retained in the second suture mount when the second needle is moved from the withdrawn position to the advanced position and returned to the withdrawn position while the second arm is at least partially retracted from the extended position.

9. The device of claim 1, wherein the first and second needles are mounted for simultaneous movement.

10. The device of claim 1, wherein the first and second arms are moveable simultaneously between withdrawn and extended positions.

11. A device for suturing an anatomic valve, the device comprising:
   an elongate body having a proximal end and a distal end;
   a first needle operatively coupled to the elongate body near the distal end of the elongate body for movement between a withdrawn position and an advanced position;
   a first arm attached to the elongate body near the distal end of the elongate body for movement between a retracted position and an extended position, the first arm being at a greater angle with the elongate body in the extended position than in the retracted position, the first arm comprising a suture mount for releasably retaining a suture portion, the suture mount being positioned on the first arm such that the first needle retrieves the suture portion retained in the suture mount when the first needle is moved from the withdrawn position to the advanced position and returned to the withdrawn position, a tissue-piercing structure of the first needle being received within the first arm when the first arm is in the retracted position and the first needle is in the advanced position; and
   at least a second arm and at least a second needle,
   wherein a recess is defined between the elongate body and the first arm, the recess being sized and shaped to receive a leaflet of a valve between the distal end of the elongate body and the first arm without damaging the leaflet;
   wherein the first needle is configured to penetrate the leaflet of the valve as the first needle moves to the advanced position when the leaflet is between the distal end of the elongate body and the first arm.

12. The device of claim 11, wherein the recess is sized and shaped to retain the leaflet between the elongate body and the first arm when the first arm is in the retracted position without damaging the leaflet.

13. The device of claim 11, wherein the suture mount is positioned on the first arm such that the first needle retrieves the suture portion retained in the suture mount when the first needle is moved from the withdrawn position to the advanced position and returned to the withdrawn position while the first arm is in the retracted position.

14. The device of claim 11, wherein the second needle is operatively coupled to the elongate body near the distal end of the elongate body for movement between a withdrawn position and an advanced position.

15. The device of claim 14, wherein the second arm is attached to the elongate body near the distal end of the elongate body for movement between a retracted position and an extended position, the second arm being at a greater angle with the elongate body in the extended position than in the retracted position, the second arm comprising a second suture mount for releasably retaining a second suture portion, the second suture mount being positioned on the second arm such that the second needle retrieves the second suture portion retained in the second suture mount when the second needle is moved from the withdrawn position to the advanced position and returned to the withdrawn position.

16. The device of claim 15, wherein a tissue-piercing structure of the second needle is received within the second arm when the second arm is in the retracted position and the second needle is in the advanced position.

17. The device of claim 15, wherein a second recess is defined between the elongate body and the second arm, the second recess being sized and shaped to retain a second leaflet between the elongate body and the second arm when the second arm is in the retracted position without damaging the second leaflet.

18. The device of claim 15, wherein the second suture mount is positioned on the second arm such that the second needle retrieves the suture portion retained in the second suture mount when the second needle is moved from the withdrawn position to the advanced position and returned to the withdrawn position while the second arm is in the retracted position.

19. The device of claim 11, wherein the first and second needles are mounted for simultaneous movement.

20. The device of claim 11, wherein the first and second arms are moveable simultaneously between withdrawn and extended positions.

* * * * *

UNITED STATES PATENT AND TRADEMARK OFFICE
CERTIFICATE OF CORRECTION

PATENT NO. : 11,166,712 B2
APPLICATION NO. : 16/370198
DATED : November 9, 2021
INVENTOR(S) : Nobles et al.

It is certified that error appears in the above-identified patent and that said Letters Patent is hereby corrected as shown below:

On the Title Page

Item (73) Assignee, delete "(VG)" and insert -- (VI) --.

Signed and Sealed this
First Day of March, 2022

Drew Hirshfeld
*Performing the Functions and Duties of the*
*Under Secretary of Commerce for Intellectual Property and*
*Director of the United States Patent and Trademark Office*